US009572613B2

(12) United States Patent
Truckai et al.

(10) Patent No.: US 9,572,613 B2
(45) Date of Patent: Feb. 21, 2017

(54) BONE TREATMENT SYSTEMS AND METHODS

(71) Applicant: DFINE, INC., South Jordan, UT (US)

(72) Inventors: Csaba Truckai, Saratoga, CA (US); John Shadduck, Tiburon, CA (US)

(73) Assignee: DFine, Inc., South Jordan, UT (US)

( * ) Notice: Subject to any disclaimer, the term of this patent is extended or adjusted under 35 U.S.C. 154(b) by 0 days.

(21) Appl. No.: 14/886,633

(22) Filed: Oct. 19, 2015

(65) Prior Publication Data

US 2016/0106488 A1  Apr. 21, 2016

Related U.S. Application Data

(60) Continuation of application No. 14/304,300, filed on Jun. 13, 2014, now Pat. No. 9,161,797, which is a
(Continued)

(51) Int. Cl.
*A61B 17/58* (2006.01)
*A61B 17/60* (2006.01)
(Continued)

(52) U.S. Cl.
CPC .......... *A61B 17/8816* (2013.01); *A61B 17/88* (2013.01); *A61B 17/8822* (2013.01); *A61B 17/8836* (2013.01); *A61B 17/8811* (2013.01)

(58) Field of Classification Search
CPC combination set(s) only.
See application file for complete search history.

(56) References Cited

U.S. PATENT DOCUMENTS 3,349,840 A  10/1967 Tope et al.
3,376,999 A  4/1968 De Hart et al.
(Continued)

FOREIGN PATENT DOCUMENTS

EP  0361408  4/1990
EP  0581387  2/1994
(Continued)

OTHER PUBLICATIONS

B. Heublein, R. Rohde, V. Kaese, M. Niemeyer, W. Hartung, A. Haverich, "Biocorrosion of magnesium alloys: a new principle in cardiovascular implant technology?", Heart, 2003; 89:651-656.
(Continued)

*Primary Examiner* — Sameh Boles
(74) *Attorney, Agent, or Firm* — Stoel Rives LLP

(57) ABSTRACT

Systems and methods for treating bone, such as vertebral compression fractures are disclosed. A method includes controllably applying energy to a bone cement volume outside of a patient's body to selectively accelerate the polymerization rate of the bone fill material volume prior to introduction into a bone. The method further includes sequentially introducing a plurality of cement carrying structures with the accelerated polymerization rate bone cement volume into the bone. A system for use in the method includes at least one elongated cement-carrying structure sized to carry a bone cement volume therein and an energy source operatively coupleable to the cement-carrying structure. The energy source applies energy to the bone cement volume to selectively accelerate a polymerization rate thereof. An elongated injector insertable into the bone has a passageway that removably receives the elongated cement-carrying structure to allow delivery of the accelerated polymerization rate bone cement into the bone.

8 Claims, 25 Drawing Sheets

Related U.S. Application Data division of application No. 13/858,672, filed on Apr. 8, 2013, now Pat. No. 8,764,761, which is a division of application No. 12/112,477, filed on Apr. 30, 2008, now Pat. No. 8,430,887.

(60) Provisional application No. 60/926,936, filed on Apr. 30, 2007.

(51) Int. Cl.
*A61F 2/00* (2006.01)
*A61B 17/88* (2006.01)

(56) References Cited

U.S. PATENT DOCUMENTS

| | | |
|---|---|---|
| 3,739,947 A | 6/1973 | Baumann et al. |
| 4,194,505 A | 3/1980 | Schmitz |
| 4,250,887 A | 2/1981 | Dardik et al. |
| 4,265,618 A | 5/1981 | Herskovitz et al. |
| 4,280,233 A | 7/1981 | Raab |
| 4,294,251 A | 10/1981 | Greenwald et al. |
| 4,338,925 A | 7/1982 | Miller |
| 4,377,168 A | 3/1983 | Rzasa et al. |
| 4,416,995 A | 11/1983 | Amaral |
| 4,492,576 A | 1/1985 | Dragan |
| 4,735,625 A | 4/1988 | Davidson |
| 4,772,287 A | 9/1988 | Ray et al. |
| 4,808,184 A | 2/1989 | Tepic |
| 4,849,223 A | 7/1989 | Pratt et al. |
| 4,959,104 A | 9/1990 | Iino et al. |
| 4,963,151 A | 10/1990 | Ducheyne et al. |
| 4,969,888 A | 11/1990 | Scholten et al. |
| 4,969,906 A | 11/1990 | Kronman |
| 4,973,168 A | 11/1990 | Chan |
| 5,037,437 A | 8/1991 | Matsen |
| 5,051,482 A | 9/1991 | Tepic |
| 5,108,404 A | 4/1992 | Scholten |
| 5,130,950 A | 7/1992 | Orban et al. |
| 5,145,250 A | 9/1992 | Planck et al. |
| 5,190,524 A | 3/1993 | Wex |
| 5,190,525 A | 3/1993 | Oswald et al. |
| 5,431,185 A | 7/1995 | Shannon et al. |
| 5,431,654 A | 7/1995 | Nic |
| 5,514,135 A | 5/1996 | Earle |
| 5,531,683 A | 7/1996 | Kriesel et al. |
| 5,542,928 A | 8/1996 | Evans et al. |
| 5,574,075 A | 11/1996 | Draenert |
| 5,674,394 A | 10/1997 | Whitmore |
| 5,679,299 A | 10/1997 | Gilbert et al. |
| 5,688,252 A | 11/1997 | Matsuda et al. |
| 5,693,099 A | 12/1997 | Harle |
| 5,695,478 A | 12/1997 | Haindl |
| 5,713,857 A | 2/1998 | Grimard et al. |
| 5,788,711 A | 8/1998 | Lehner et al. |
| 5,810,773 A | 9/1998 | Pesnicak |
| 5,814,681 A | 9/1998 | Hino et al. |
| 5,824,084 A | 10/1998 | Muschler |
| 5,865,798 A | 2/1999 | Grimard et al. |
| 5,899,881 A | 5/1999 | Grimard et al. |
| 5,954,716 A | 9/1999 | Sharkey et al. |
| 6,048,346 A | 4/2000 | Reiley et al. |
| 6,075,067 A | 6/2000 | Lidgren |
| 6,120,174 A | 9/2000 | Hoag et al. |
| 6,122,549 A | 9/2000 | Sharkey et al. |
| 6,171,312 B1 | 1/2001 | Beaty |
| 6,231,615 B1 | 5/2001 | Preissman |
| 6,235,043 B1 | 5/2001 | Reiley et al. |
| 6,236,020 B1 | 5/2001 | Friedman |
| 6,241,734 B1 | 6/2001 | Scribner |
| 6,248,110 B1 | 6/2001 | Reiley et al. |
| 6,261,289 B1 | 7/2001 | Levy |
| 6,264,659 B1 | 7/2001 | Ross et al. |
| 6,280,456 B1 | 8/2001 | Scribner et al. |
| 6,309,420 B1 | 10/2001 | Preissman |
| 6,312,149 B1 | 11/2001 | Sjovall et al. |
| 6,312,254 B1 | 11/2001 | Friedman |
| 6,316,885 B1 | 11/2001 | Collins et al. |
| 6,319,255 B1 | 11/2001 | Grundei et al. |
| 6,332,894 B1 | 12/2001 | Stalcup et al. |
| 6,358,254 B1 | 3/2002 | Anderson |
| 6,375,659 B1 | 4/2002 | Erbe et al. |
| 6,395,007 B1 | 5/2002 | Bhatnagar et al. |
| 6,425,923 B1 | 7/2002 | Stalcup et al. |
| 6,436,143 B1 | 8/2002 | Ross et al. |
| 6,439,439 B1 | 8/2002 | Rickard |
| 6,443,988 B2 | 9/2002 | Felt et al. |
| 6,447,514 B1 | 9/2002 | Stalcup et al. |
| 6,458,127 B1 | 10/2002 | Truckai et al. |
| 6,485,436 B1 | 11/2002 | Truckai |
| 6,524,102 B2 | 2/2003 | Davis |
| 6,558,428 B2 | 5/2003 | Park |
| 6,575,930 B1 | 6/2003 | Trombley, III et al. |
| 6,610,079 B1 | 8/2003 | Li et al. |
| 6,613,018 B2 | 9/2003 | Bagga et al. |
| 6,613,054 B2 | 9/2003 | Scribner et al. |
| 6,620,185 B1 | 9/2003 | Harvie et al. |
| 6,632,235 B2 | 10/2003 | Weikel et al. |
| 6,706,069 B2 | 3/2004 | Berger |
| 6,709,149 B1 | 3/2004 | Tepic |
| 6,712,852 B1 | 3/2004 | Chung et al. |
| 6,719,773 B1 | 4/2004 | Boucher et al. |
| 6,723,095 B2 | 4/2004 | Hammerslag |
| 6,726,691 B2 | 4/2004 | Osorio et al. |
| 6,736,537 B2 | 5/2004 | Coffeen et al. |
| 6,740,093 B2 | 5/2004 | Hochschuler et al. |
| 6,753,358 B2 | 6/2004 | Fisher et al. |
| 6,767,936 B2 | 7/2004 | Walz et al. |
| 6,783,515 B1 | 8/2004 | Miller |
| 6,814,736 B2 | 11/2004 | Reiley et al. |
| 6,832,988 B2 | 12/2004 | Sproul |
| 6,872,403 B2 | 3/2005 | Pienkowski et al. |
| 6,899,713 B2 | 5/2005 | Shaolian et al. |
| 6,929,640 B1 | 8/2005 | Underwood |
| 6,958,061 B2 | 10/2005 | Truckai et al. |
| 6,964,667 B2 | 11/2005 | Shaolian et al. |
| 6,979,341 B2 | 12/2005 | Scribner et al. |
| 6,979,352 B2 | 12/2005 | Reynolds |
| 6,985,061 B2 | 1/2006 | Hafskjold et al. |
| 7,008,433 B2 | 3/2006 | Voellmicke et al. |
| 7,044,954 B2 | 5/2006 | Reiley |
| 7,048,720 B1 | 5/2006 | Thorne, Jr. et al. |
| 7,048,743 B2 | 5/2006 | Miller et al. |
| 7,073,936 B1 | 7/2006 | Jonsson |
| 7,081,125 B2 | 7/2006 | Edwards et al. |
| 7,108,696 B2 | 9/2006 | Daniel et al. |
| 7,112,201 B2 | 9/2006 | Truckai et al. |
| 7,115,163 B2 | 10/2006 | Zimmermann |
| 7,153,306 B2 | 12/2006 | Ralph et al. |
| 7,153,307 B2 | 12/2006 | Scribner et al. |
| 7,160,020 B2 | 1/2007 | Sand |
| 7,166,121 B2 | 1/2007 | Reiley et al. |
| 7,175,336 B2 | 2/2007 | Voellmicke et al. |
| 7,191,285 B2 | 3/2007 | Scales |
| 7,226,481 B2 | 6/2007 | Kuslich |
| 7,241,303 B2 | 7/2007 | Reiss et al. |
| 7,252,672 B2 | 8/2007 | Yetkinler |
| 7,259,210 B2 | 8/2007 | Puckett et al. |
| 7,261,720 B2 | 8/2007 | Stevens et al. |
| 7,273,523 B2 | 9/2007 | Wenz |
| 7,306,598 B2 | 12/2007 | Truckai et al. |
| 7,431,763 B2 | 10/2008 | Zimmermann |
| 7,510,579 B2 | 3/2009 | Preissman |
| 7,559,932 B2 | 7/2009 | Truckai et al. |
| 7,662,133 B2 | 2/2010 | Scarborough et al. |
| 7,678,116 B2 | 3/2010 | Truckai et al. |
| 7,682,378 B2 | 3/2010 | Truckai et al. |
| 7,708,733 B2 | 5/2010 | Sanders et al. |
| 7,717,918 B2 | 5/2010 | Truckai et al. |
| 7,722,620 B2 | 5/2010 | Truckai et al. |
| 7,722,624 B2 | 5/2010 | Boucher et al. |
| 7,744,270 B2 | 6/2010 | Plishka et al. |
| 8,066,712 B2 | 11/2011 | Truckai et al. |
| 8,070,753 B2 | 12/2011 | Truckai et al. |

(56) References Cited

U.S. PATENT DOCUMENTS

| | | | |
|---|---|---|---|
| 8,192,442 B2 | 6/2012 | Truckai et al. |
| 8,267,571 B2 | 9/2012 | Johansson et al. |
| 8,308,340 B2 | 11/2012 | Ferrante et al. |
| 8,348,955 B2 | 1/2013 | Truckai et al. |
| 8,430,887 B2 | 4/2013 | Truckai et al. |
| 8,540,723 B2 | 9/2013 | Shadduck et al. |
| 8,562,620 B2 | 10/2013 | Truckai et al. |
| 8,764,761 B2 | 7/2014 | Truckai et al. |
| 9,161,797 B2 | 10/2015 | Truckai et al. |
| 9,180,416 B2 | 11/2015 | Phan et al. |
| 2001/0011190 A1 | 8/2001 | Park |
| 2002/0068974 A1 | 6/2002 | Kuslich et al. |
| 2002/0147497 A1 | 10/2002 | Belef et al. |
| 2002/0165582 A1 | 11/2002 | Porter |
| 2002/0191487 A1 | 12/2002 | Sand |
| 2003/0032929 A1 | 2/2003 | McGuckin |
| 2003/0130738 A1 | 7/2003 | Hovda et al. |
| 2003/0220648 A1 | 11/2003 | Osorio et al. |
| 2003/0233096 A1 | 12/2003 | Osorio et al. |
| 2004/0024410 A1 | 2/2004 | Olson |
| 2004/0083002 A1 | 4/2004 | Belef et al. |
| 2004/0110285 A1 | 6/2004 | Lendlein |
| 2004/0138748 A1 | 7/2004 | Boyer, II et al. |
| 2004/0172132 A1 | 9/2004 | Ginn |
| 2004/0180986 A1 | 9/2004 | Bellare et al. |
| 2004/0186576 A1 | 9/2004 | Biscup et al. |
| 2004/0193171 A1 | 9/2004 | DiMauro et al. |
| 2004/0228898 A1 | 11/2004 | Ross et al. |
| 2004/0267272 A1 | 12/2004 | Henniges |
| 2005/0010231 A1 | 1/2005 | Myers |
| 2005/0015148 A1 | 1/2005 | Jansen et al. |
| 2005/0113843 A1 | 5/2005 | Arramon |
| 2005/0180806 A1 | 8/2005 | Green et al. |
| 2005/0209595 A1 | 9/2005 | Karmon |
| 2005/0222681 A1 | 10/2005 | Richley et al. |
| 2005/0245938 A1 | 11/2005 | Kochan |
| 2005/0251149 A1 | 11/2005 | Wenz |
| 2006/0000284 A1 | 1/2006 | Sherman et al. |
| 2006/0052743 A1 | 3/2006 | Reynolds |
| 2006/0052794 A1 | 3/2006 | McGill et al. |
| 2006/0074433 A1 | 4/2006 | McGill et al. |
| 2006/0079834 A1 | 4/2006 | Tennican et al. |
| 2006/0079905 A1 | 4/2006 | Beyar et al. |
| 2006/0095138 A1 | 5/2006 | Truckai et al. |
| 2006/0100635 A1 | 5/2006 | Reiley et al. |
| 2006/0106459 A1 | 5/2006 | Truckai et al. |
| 2006/0122614 A1 | 6/2006 | Truckai et al. |
| 2006/0122622 A1 | 6/2006 | Truckai et al. |
| 2006/0122623 A1 | 6/2006 | Truckai et al. |
| 2006/0150862 A1 | 7/2006 | Zhao et al. |
| 2006/0264967 A1 | 11/2006 | Ferreyro et al. |
| 2007/0027230 A1 | 2/2007 | Beyar et al. |
| 2007/0112299 A1 | 5/2007 | Smit et al. |
| 2007/0118144 A1 | 5/2007 | Truckai et al. |
| 2007/0162043 A1 | 7/2007 | Truckai et al. |
| 2007/0185231 A1 | 8/2007 | Liu et al. |
| 2007/0191858 A1 | 8/2007 | Truckai et al. |
| 2007/0191964 A1 | 8/2007 | Preissman |
| 2007/0233148 A1 | 10/2007 | Truckai et al. |
| 2008/0065083 A1 | 3/2008 | Truckai et al. |
| 2008/0103505 A1 | 5/2008 | Fransen |
| 2008/0188858 A1 | 8/2008 | Luzzi et al. |
| 2008/0195112 A1 | 8/2008 | Liu et al. |
| 2008/0200916 A1* | 8/2008 | Murphy ............ A61B 17/8822 606/94 |
| 2009/0024161 A1 | 1/2009 | Bonutti et al. |
| 2009/0062808 A1 | 3/2009 | Wolf, II |
| 2009/0093550 A1 | 4/2009 | Rolfes et al. |
| 2009/0093818 A1 | 4/2009 | Baroud |
| 2009/0171362 A1 | 7/2009 | Schaeffer |
| 2009/0281549 A1 | 11/2009 | Dixon |
| 2010/0091606 A1 | 4/2010 | Kwan |
| 2010/0110436 A1 | 5/2010 | Chandler et al. |
| 2010/0168271 A1 | 7/2010 | Beyar et al. |

FOREIGN PATENT DOCUMENTS

| | | |
|---|---|---|
| EP | 0701824 | 3/1996 |
| EP | 1190681 | 3/2002 |
| EP | 1366774 | 12/2003 |
| JP | 2002-153491 | 5/2002 |
| JP | 2004-500952 | 1/2004 |
| JP | 2004-527311 | 9/2004 |
| WO | WO 02/058592 | 8/2002 |
| WO | WO 02/064062 | 8/2002 |
| WO | WO 02/087416 | 11/2002 |
| WO | WO 2004/075954 | 9/2004 |
| WO | WO 2006/031490 | 3/2006 |
| WO | WO 2006/062916 | 6/2006 |
| WO | WO 2006/062939 | 6/2006 |
| WO | WO 2006/090379 | 8/2006 |
| WO | WO 2006/130491 | 12/2006 |
| WO | WO 2007/028120 | 3/2007 |
| WO | WO 2007/148336 | 12/2007 |
| WO | WO 2008/001385 | 1/2008 |
| WO | WO 2008/097855 | 8/2008 |
| WO | WO 2008/124533 | 10/2008 |
| WO | WO 2009/108893 | 9/2009 |

OTHER PUBLICATIONS

Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.

Furderer S, Anders M, Schwindling B, Salick M, Duber C, Wenda K, Urban R, Gluck M, Eysel P., "Vertebral body stenting. A method for repositioning and augmenting vertebral compression fractures", Orthopade. Apr. 2002; 31(4):356-61, Abstract.

Exam Report for EPO App. 05 848 386.8 dated Sep. 18, 2009 in 5 pgs.

International Search Report and Written Opinion mailed on Apr. 22, 2010 in PCT Application No. PCT/US2009/03559.

International Search Report and Written Opinion, mailing date Jun. 17, 2009, PCT/US2008/052821.

International Search Report, dated Sep. 24, 2009, PCT/US2008/061911, 15 pgs.

International Search Report, mailing date Apr. 16, 2007, PCT/US2006/034409.

International Search Report, mailing date May 31, 2006, PCT/US2005/044055, 4 pg.

International Search Report, mailing date Jun. 20, 2006, PCT/US2005/043984, 2 pg.

* cited by examiner

BONE TREATMENT SYSTEMS AND METHODS

CROSS-REFERENCE TO RELATED APPLICATIONS

This application is a continuation of U.S. application Ser. No. 14/304,300, filed on Jun. 13, 2014, now U.S. Pat. No. 9,161,797, which is a divisional application of U.S. application Ser. No. 13/858,672, filed on Apr. 8, 2013, now U.S. Pat. No. 8,764,761, which is a divisional application of U.S. application Ser. No. 12/112,477, filed on Apr. 30, 2008, now U.S. Pat. No. 8,430,887, which claims the benefit of U.S. Provisional Application No. 60/926,936, filed on Apr. 30, 2007. The entire contents of each of these applications are hereby incorporated by reference and should be considered a part of this specification. This application is also related to the following U.S. Patent Applications: application Ser. No. 11/209,035 filed Aug. 22, 2005; Provisional App. No. 60/842,805 filed Sep. 7, 2006, titled *Bone Treatment Systems and Methods*; and Provisional App. No. 60/713,521 filed Sep. 1, 2005. The entire contents of all of the above applications are hereby incorporated by reference and should be considered a part of this specification.

BACKGROUND OF THE INVENTION

Field of the Invention

The present invention relates to bone cement injection systems, and in certain embodiments provides a system for controlling the acceleration of polymerization of bone cement prior to delivery of the bone cement into a bone.

Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from the aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be forced into the cancellous bone, the technique requires high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004. Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg. Soc. Vol. 35, No. 5 (May 2004) pp. 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al, "Asymptomatic diffuse pulmonary embolism caused by acrylic cement: an unusual complication of percutaneous vertebroplasty", Ann. Rheum. Dis. 2003; 62:85-86. The vapors from PMMA preparation and injection also are cause for concern. See Kirby, B, et al., "Acute bronchospasm due to exposure to polymethylmethacrylate vapors during percutaneous vertebroplasty", Am. J. Roentgenol. 2003; 180:543-544.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which crushes and compacts cancellous bone. Expansion of the balloon under high pressures close to the cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide bone cements and methods for use in the treatment of vertebral compression fractures to provide a greater degree of control over the introduction of cement and to provide better outcomes. The present invention meets this need and provides several other advantages in a novel and nonobvious manner.

SUMMARY OF THE INVENTION

Certain embodiments of the invention provide bone cement injectors and control systems that allow for vertebroplasty procedures that inject cement having a substantially constant viscosity over an extended cement injection interval.

In some embodiments, a computer controller is provided to control cement flow parameters in the injector and energy delivery parameters for selectively accelerating polymerization of bone cement before the cement contacts the patient's body.

In accordance with one embodiment, a method of treating a bone is provided. The method comprises providing a plurality of cement carrying structures, each structure carrying a mixed bone cement volume having a predetermined polymerization rate at which the bone cement polymerizes to a selected endpoint. The method further comprises controllably applying energy from an energy source to the bone cement volume outside of a patient's body to selectively accelerate the polymerization rate of the bone cement volume prior to introduction of the bone cement into the bone and sequentially introducing the mixed bone cement volumes with said accelerated polymerization rate into the bone.

In accordance with another embodiment, a method of treating a vertebra is provided. The method comprises providing at least one elongated structure carrying a mixed bone fill material and controllably applying energy from an energy source to the mixed bone fill material to selectively accelerate polymerization of the bone fill material outside of a patient's body. The method further comprises inserting at least a portion of an elongated injector into a vertebral body, removably inserting at least a portion of the at least one elongated structure into the elongated injector, and delivering the mixed bone fill material with said accelerated polymerization into the vertebral body.

In accordance with another embodiment, a system for treating a vertebra is provided. The system comprises at least one elongated cement-carrying structure having an interior space for receiving a bone fill material and an energy source operatively coupleable to the cement-carrying structure outside of a patient's body, the energy source configured to apply energy to the bone fill material to selectively accelerate a polymerization rate of the bone fill material. The system further comprises an elongated injector, at least a portion of which is insertable into a vertebral body, the elongated injector comprising a passageway sized to removably receive at least a portion of the elongated cement-carrying structure so as to allow delivery of the bone fill material with said accelerated polymerization rate through the injector into the vertebral body.

In accordance with another embodiment, a system for treating bone is provided. The system comprises an elongated injector, at least a portion of which insertable into a bone and at least one cement-carrying structure configured to contain a volume of a mixed bone fill material, the cement carrying structure releasably coupleable to the injector. The system further comprises at least one housing member comprising an energy emitter and sized to removably receive at least a portion of the cement-carrying structure, the energy emitter configured to apply energy to the bone fill material outside of a patient's body when the cement-carrying structure is coupled to the housing to thereby selectively accelerate the polymerization of the mixed bone fill material.

In accordance with still another embodiment, a kit for treating bone is provided. The kit comprises a plurality of elongated cement-carrying devices configured to receive a volume of mixed bone fill material therein, an elongated bone fill material injector, and at least one housing configured to removably receive at least one of the plurality of elongated cement-carrying devices in a passage thereof. The housing comprises an energy emitter configured to apply energy to the mixed bone fill material in the cement-carrying device disposed in the housing to selectively accelerate the polymerization rate of a selected volume of the mixed bone fill material to a selected endpoint. The kit further comprises an energy source coupleable to the energy emitter to deliver energy thereto.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE PREFERRED EMBODIMENTS

Figure 1:
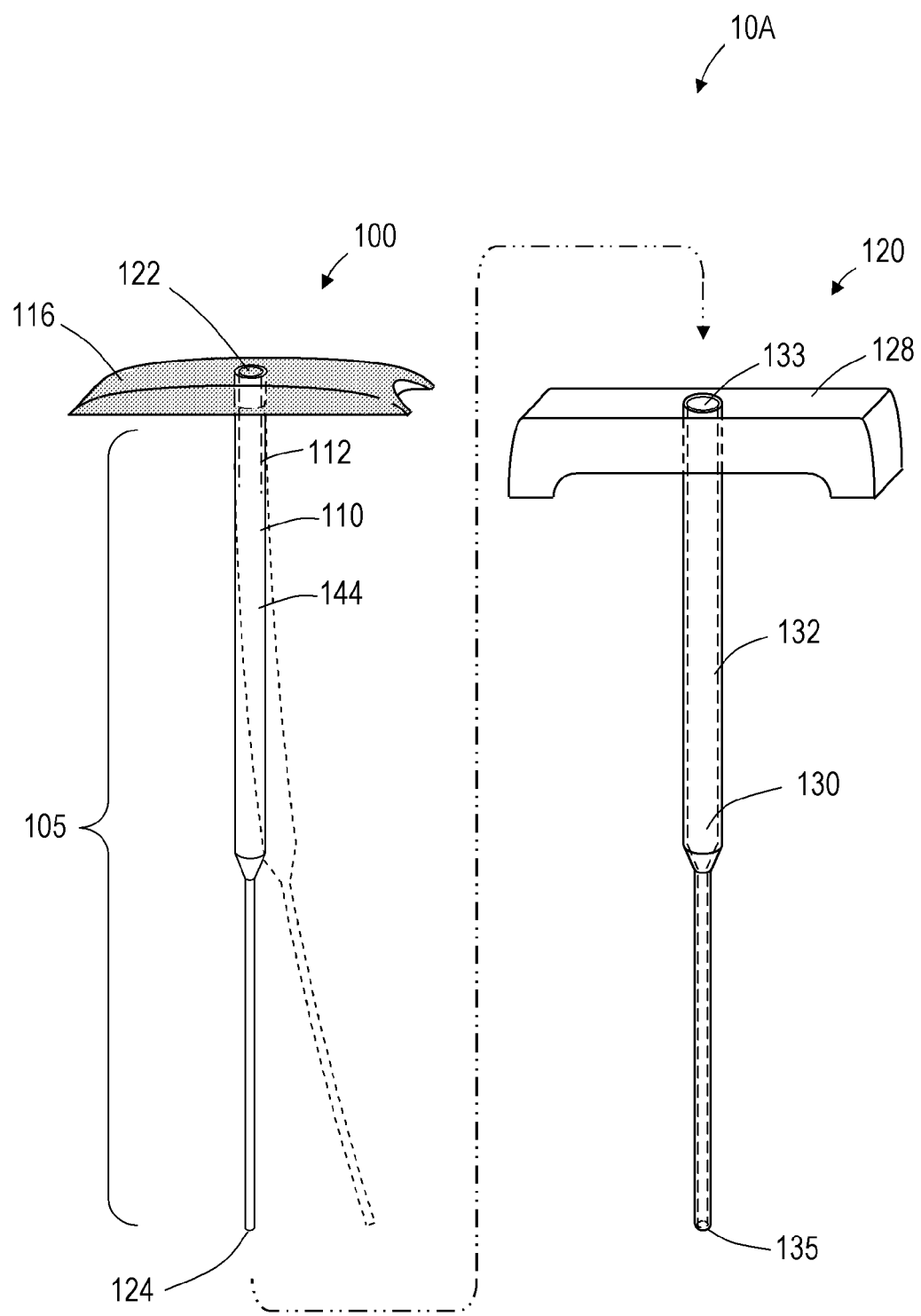
FIG. 1 is a schematic perspective view of one embodiment of a bone cement injection system.

For purposes of understanding the principles of the invention, reference will now be made to the embodiments illustrated in the drawings and accompanying text that describe certain embodiments of the invention. As background, in certain embodiments a vertebroplasty procedure would insert the system of FIGS. 1-5D through a pedicle of a vertebra, or by a parapedicular approach, for accessing the osteoporotic cancellous bone. The initial aspects of the procedure are similar to a conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician uses a scalpel to make a 1 to 5 mm skin incision over each targeted pedicle. Thereafter, the introducer is advanced through the pedicle into the anterior region of the vertebral body, which typically is the region of greatest compression and fracture. The physician confirms the introducer path posterior to the pedicle, through the pedicle and within the vertebral body by anteroposterior and lateral X-Ray projection fluoroscopic views. The introduction of infill material as described below can be imaged several times, or continuously, during the treatment depending on the imaging method.

DEFINITIONS

"Bone cement, bone fill or fill material, infill material or composition" includes its ordinary meaning and is defined as any material for infilling a bone that includes an in-situ hardenable material or that can be infused with a hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

"Substantially" or "substantial" mean largely but not entirely. For example, substantially may mean about 50% to about 99.999%, about 80% to about 99.999% or about 90% to about 99.999%.

"Vertebroplasty" includes its ordinary meaning and means any procedure wherein fill material is delivered into the interior of a vertebra.

"Osteoplasty" includes its ordinary meaning and means any procedure wherein fill material is delivered into the interior of a bone.

Figure 2:
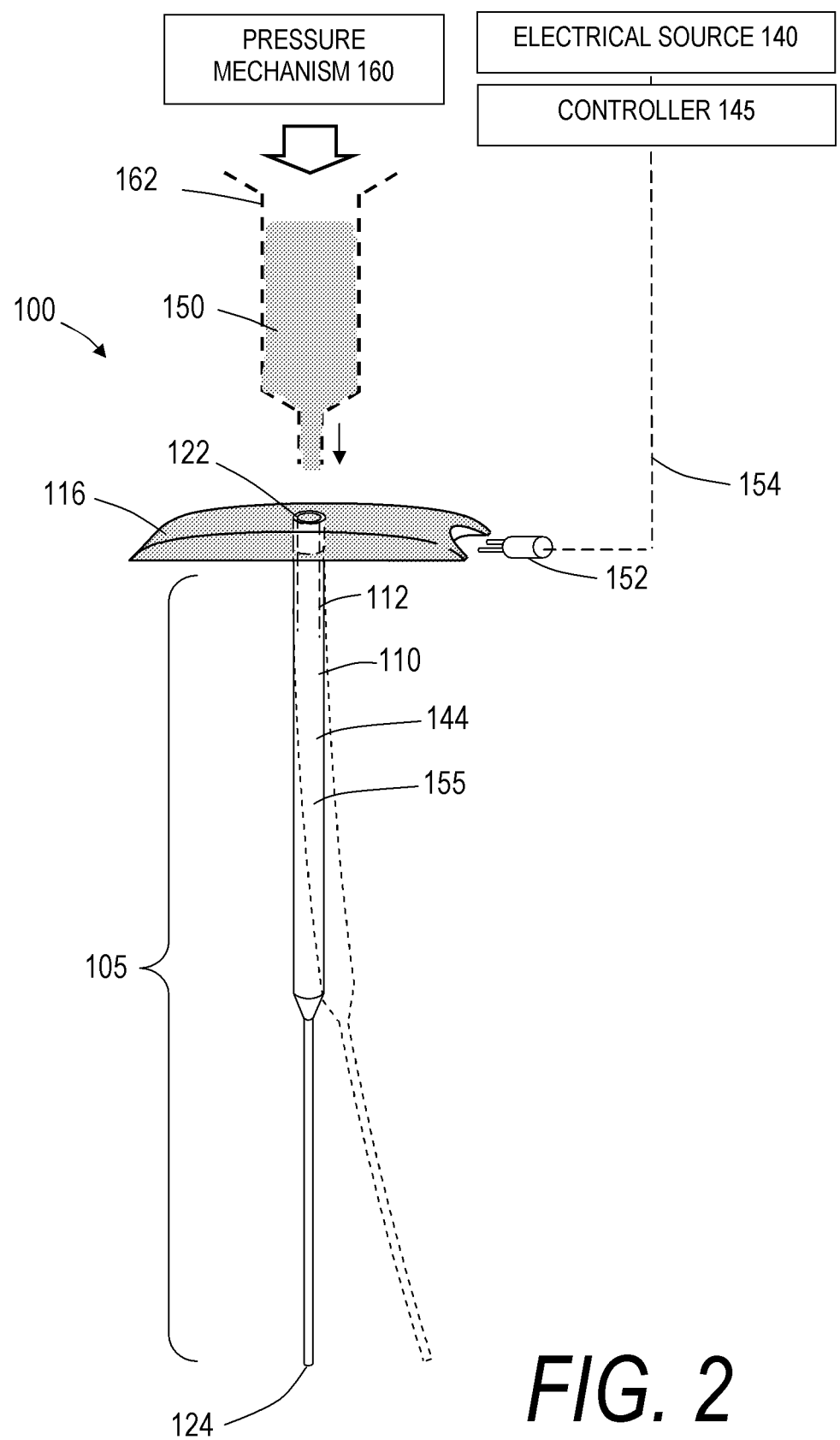
FIG. 2 is another schematic view of the bone cement injection system of FIG. 1.

In one embodiment, as depicted in FIG. 1, a system 10A is shown that includes a first component 100 including a bone cement-carrying structure 105 that can have an elongated sleeve 110. The elongated sleeve 110 can be of a thin-wall polymer or metal and defines an interior space or channel 112 into which a volume of a pre-polymerized bone cement 150 mixture can be loaded (FIG. 2). In one embodiment, the pre-polymerized bone cement mixture can be an uncured bone cement mixture. In another embodiment, the pre-polymerized bone cement mixture can be a partially cured bone cement mixture. The first component 100 optionally includes a proximal handle or grip portion 116 with the cement-carrying structure 105 being coupleable with or removably receivable in a second component or bone cement injector 120, described below. As can be seen in FIG. 1, the elongated sleeve 110 and interior space or channel 112 can have an open proximal end 122 for loading cement 150 into the structure 105 and an open distal outlet 124. The open proximal end 122 can, in one embodiment, have an interlock element (e.g., a Luer fitting) for coupling with a cement source, such as a syringe, for loading cement 150 into the structure 105.

The cement-carrying structure 105 and its interior channel 112 can in certain embodiments be round or polygonal in cross-section, have a constant diameter along its length or a stepped diameter, as shown in FIG. 1, or can have a flattened shape to provide a ribbon-like volume of cement therein, as described below. In one embodiment, the cement-carrying structure 105 can be a very thin walled polymer sleeve and can be transparent or translucent to allow observation of the cement. The cement-carrying structure 105 can have a capacity of at least 0.10 cc, at least 0.50 cc, at least 1.0 cc and at least 2.0 cc of bone cement.

The second component or bone cement injector 120 of the system 10A can be similar to commercially available injectors with a handle portion 128 and an elongated extension portion 130 that can be of a rigid tubular material. An interior space or receiving portion 132 in the injector 120 can be sized to at least partly receive the cement-carrying structure 105 of the first component 100 as can be seen in FIG. 1. The bone cement injector 120 and more particularly its interior space 132 with an open proximal end 133 and an open termination or outlet 135 allows for bone cement flow therethrough into the interior of a bone. As can be understood in FIG. 1, the proximal handle portions 116 and 128 of the first and second components 100, 120 can releaseably interlock using any suitable mechanism known in the art.

In another view of the embodiment as shown in FIG. 2, the first component 100 and cement-carrying structure 105 can be coupled to an energy source, such as an electrical source 140 that provides for delivery of thermal energy from an emitter mechanism 144 within the cement-carrying structure 105. In one embodiment, the thermal energy emitter 144 can be carried substantially throughout the length of the cement-carrying structure 105. In other embodiments, the thermal energy emitter 144 can be carried within a proximal region, a medial region or a distal region of the cement-carrying structure 105. The system can further include a controller 145 operatively coupled to the energy source 140. The source 140 can preferably cause thermal effects in the bone cement 150 contained in the cement-carrying structure 105 and accelerate the polymerization of the bone cement.

As depicted in FIG. 2, the bone cement 150 can have a predetermined working time for polymerizing from an initial state to a selected endpoint (e.g., predetermined endpoint) of at least 8 minutes, 10 minutes, 12 minutes, 14 minutes, 16 minutes, 18 minutes, 20 minutes, 25 minutes, 30 minutes and 40 minutes, as disclosed in co-pending Provisional Application Ser. No. 60/899,487 filed Feb. 5, 2007 and titled *Bone Treatment Systems and Methods*, the entire contents of which are hereby incorporated by reference and should be considered a part of this specification. The selected polymerization endpoint provides the bone cement 150 in a partly polymerized condition having a selected viscosity range that substantially inhibits cement extravasation. Herein, the terms 'polymerization rate' and 'working time' may be used alternatively to describe the interval in which the cement polymerizes from the initial or just-mixed state to the selected endpoint.

As can be understood from FIG. 2, the energy source can accelerate a polymerization rate of the bone cement 150 by at least 20%, 30%, 40%, 50%, 60%, 70%, 80%, 90% and 95%. In another aspect of the invention, the energy source 140 and controller 145 can accelerate the polymerization rate of the cement to the selected endpoint in less than 1 second, 5 seconds, 10 seconds, 20 seconds, 30 seconds, 45 seconds, 60 seconds and 2 minutes.

Figure 3:
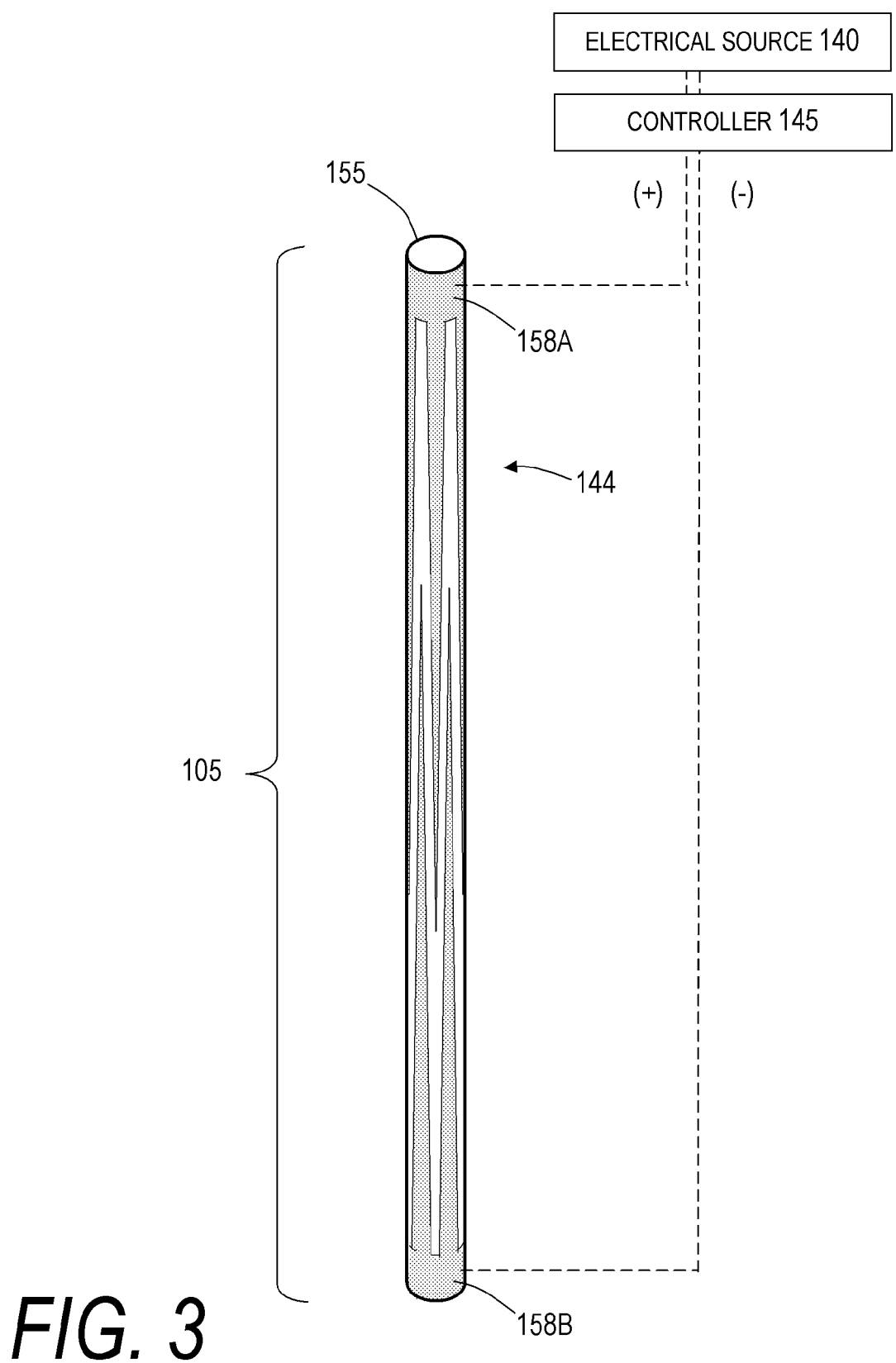
FIG. 3 is a schematic view of a thermal emitter component of the system of FIG. 1.

Referring to the embodiment illustrated in FIGS. 2 and 3, the electrical source 140 and controller 145 can be coupled to the first component 100 by an electrical connector 152 and cable 154. As can be seen in FIG. 3, the wall 155 of the cement-carrying structure 105 can carry the thermal energy emitter 144, which can include a polymeric positive temperature coefficient of resistance (PTCR) material with spaced apart interlaced surface electrodes 158A and 158B as described in co-pending Provisional Application No. 60/907,468 filed Apr. 3, 2007 titled *Bone Treatment Systems and Methods*. In this embodiment, the thermal emitter 144 and wall 155 resistively heat and cause controlled thermal effects in the cement 150 contained therein. It should be appreciated that FIG. 3 is a schematic representation of the cement-carrying structure 105 and can have any elongated or truncated shape or geometry, tapered or non-tapered form, or comprise the wall of a collapsible thin-film element, such as a bladder or balloon-like member. Further, the positive (+) and negative (−) polarity electrodes can have a spaced apart arrangement, for example a radially spaced apart arrangement, a helically spaced apart arrangement, an axially spaced apart arrangement or any combination thereof. This resistively heated PTCR material of the emitter 144 can further generate a signal that indicates flow rate, as described in Provisional Application No. 60/907,468, which in turn can be utilized by the controller 145 to modulate the energy applied to the cement 150.

As can be understood from FIGS. 1 & 2, the system 10A can further include a cement actuation mechanism or pressure mechanism 160 for moving the cement 150 through the first component 100 and/or injector 120 into the interior of a vertebra 172. The actuation mechanism 160 can be a simple piston or plunger, as in a syringe 162, as indicated in FIG. 2. Alternatively, a hydraulic fluid flow mechanism can be used to apply pressure to cement 150 in the first component 100 and/or injector 120. However, any other form of pump (e.g., a pneumatic pressure mechanism) may be used to apply pressure to the cement 150 to facilitate the flow of bone cement 150 through the component 100 and/or injector 120.

Figure 4:
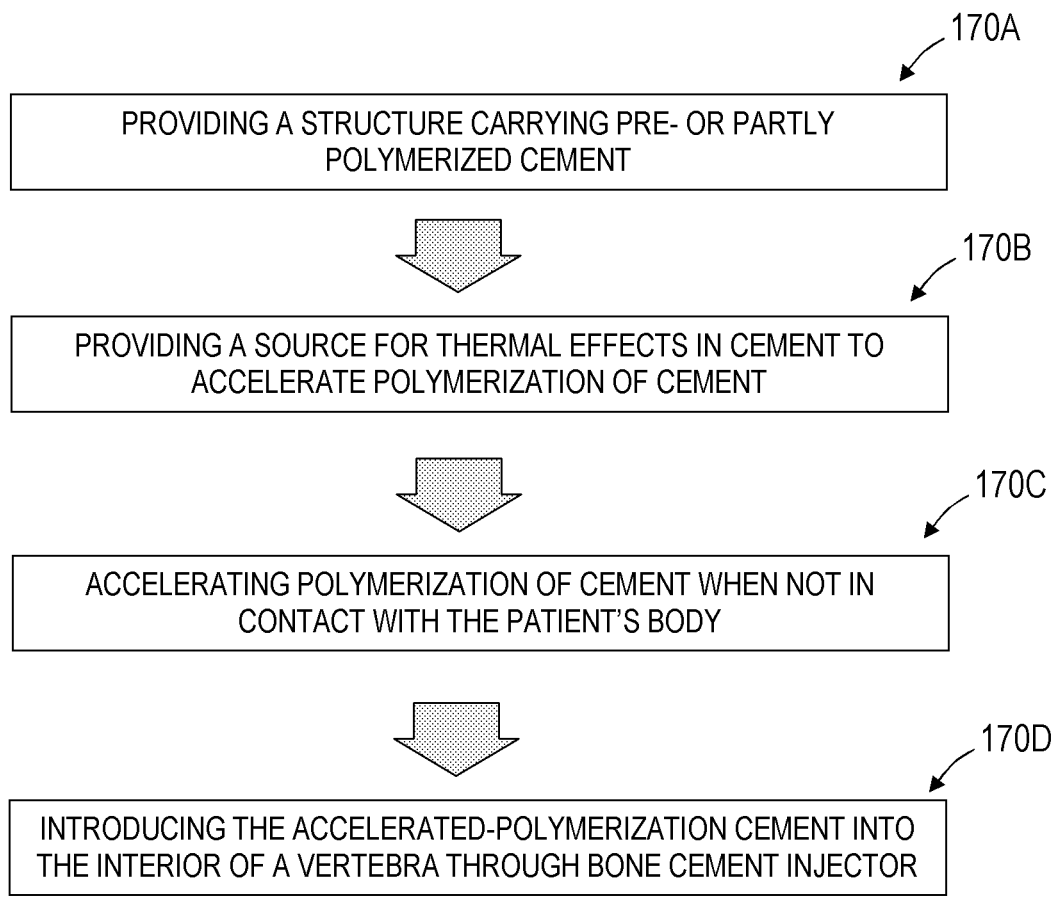
FIG. 4 is a schematic block diagram of one bone cement injection method utilizing the system of FIGS. 1-2.

Now turning to FIG. 4, a method, corresponding to one embodiment of the invention, utilizing the system 10, comprises the following steps as shown in the block diagram: (i) providing the cement-carrying structure 105 of FIGS. 1 and 2 that carries a pre-polymerized bone cement indicated at 170A; (ii) providing a source 140 for causing thermal effects in the cement 150 indicated at 170B; (iii) accelerating polymerization of the cement 150 when the cement 150 is not in contact with the patient's body indicated at 170C; and (iv) introducing the accelerated-polymerization cement 150' into the interior of a vertebra 172 thru a cement injector 120 indicated at 170D.

Figure 5A:
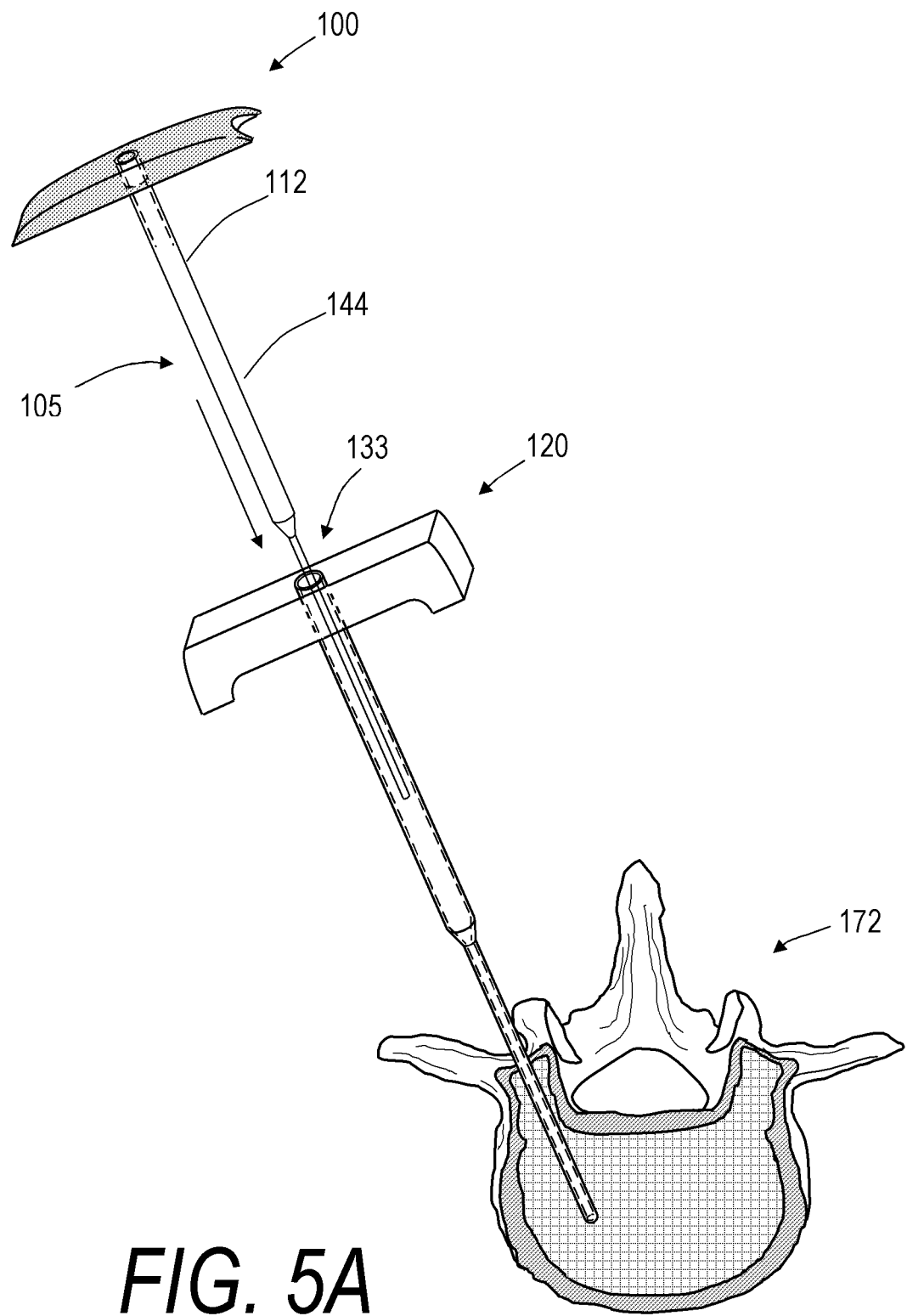
FIG. 5A is a graphical representations of a first step of one bone cement injection method.
Figure 5B:
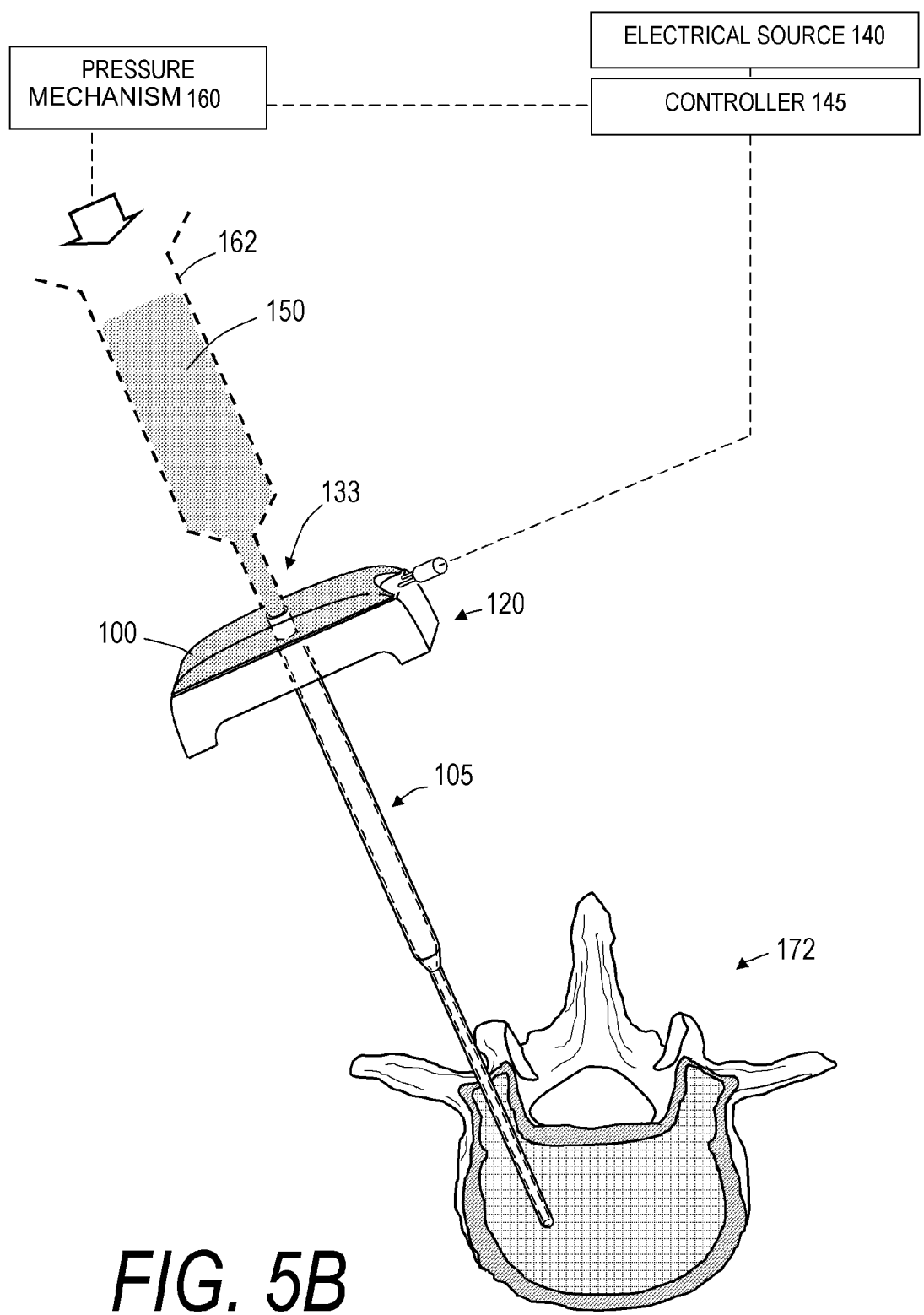
FIG. 5B is a graphical representation of a subsequent step of assembling components in one embodiment of the bone cement injection method.

FIGS. 5A-5D graphically depicts one method for delivering bone cement 150, as described in the block diagram of FIG. 4. In FIG. 5A, the bone cement injector 120 of FIG. 1 is inserted into a vertebra 172, for example by a transpedicular access or a parapedicular access. In FIG. 5A, it also can be seen that a first component 100 and cement-carrying structure 105 is prepared for introduction into the receiving portion 132 of the cement injector 120. FIG. 5B next depicts the insertion of the cement-carrying structure 105 into the receiving portion 132 of the cement injector 120 and the coupling of a source of cement 150 to a cement-carrying structure 105. In the illustrated embodiment, the source of bone cement 150 is a syringe 162.

Figure 5C:
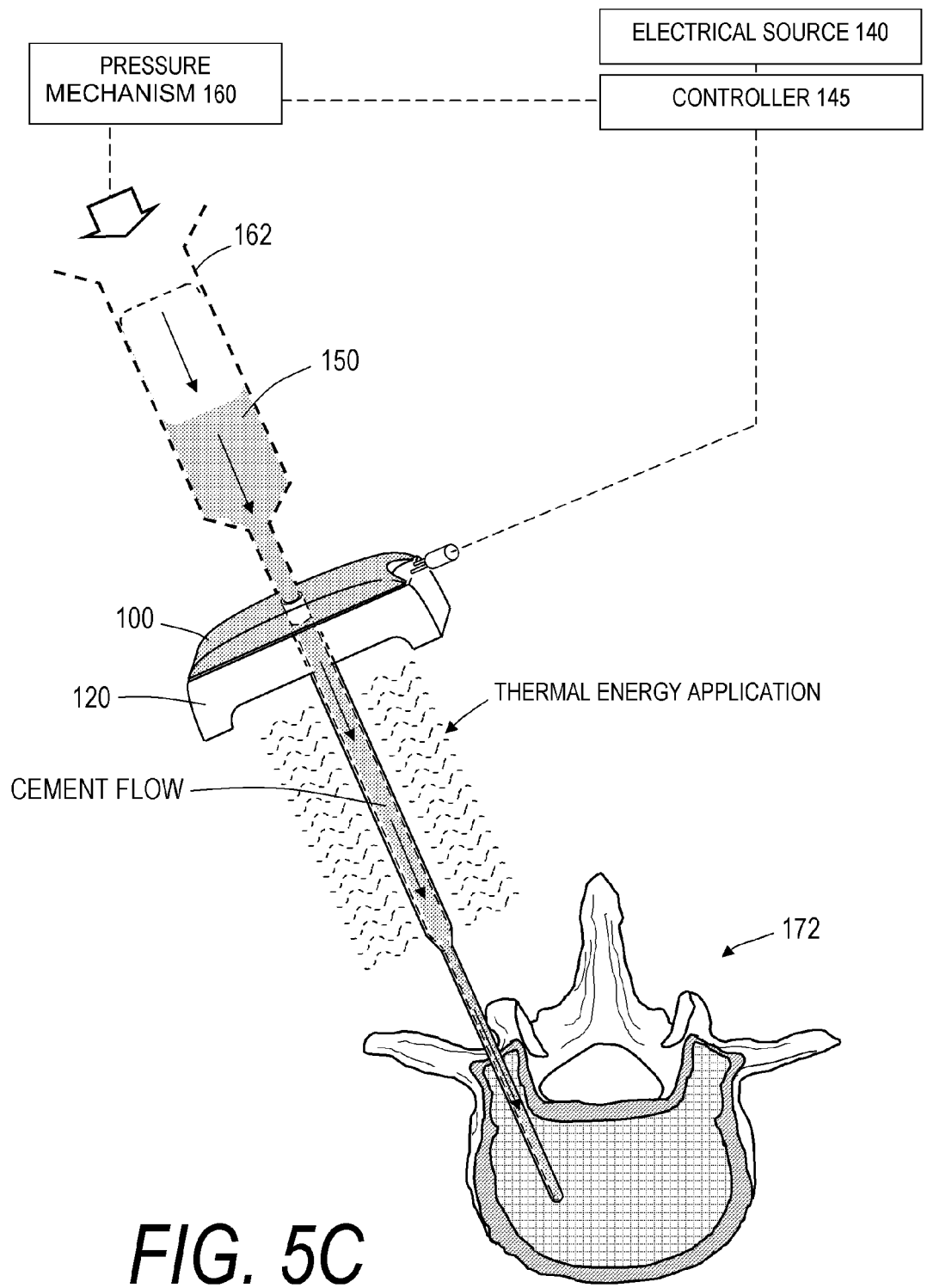
FIG. 5C is a graphical representation of a subsequent step of applying energy to cement and injecting cement into a vertebra according to bone cement injection method.
Figure 5D:
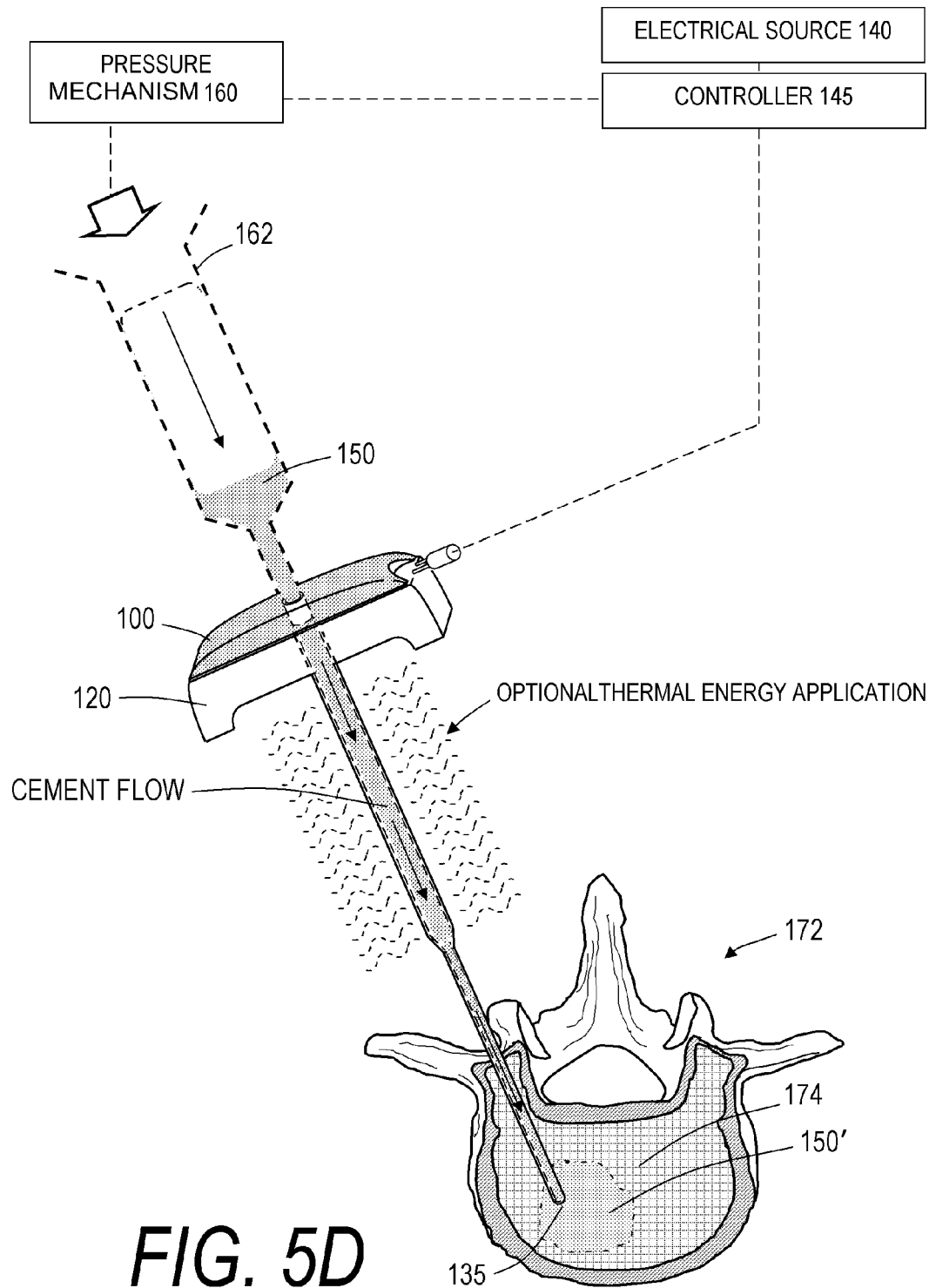
FIG. 5D is another schematic view of the injecting step in the bone cement injection method.

FIG. 5C next depicts another step in one embodiment in which a flow of bone cement 150 is injected from the syringe 162 into the channel 112 of the cement-carrying structure 105. FIG. 5C further depicts the actuation of the electrical source 140 and the controller 145 to thereby heat the emitter 144 and apply thermal energy from the emitter 144 and cement-carrying structure 105 to the flow of cement 150 to thereby accelerate polymerization of the cement flow through the thermal energy emitter 144 and cement-carrying structure 105. FIG. 5D next depicts the flow of 'accelerated polymerization' bone cement 150' into the interior 174 cancellous bone of the vertebra 172 from the outlet 135 of the cement injector 120. As depicted in FIG. 5D, the method provides a modified volume of cement 150' that first contacts bone having an 'accelerated-polymerization' state within a selected viscosity range that substantially prevents cement extravasation. As can be seen in FIGS. 5C-5D, the thermal energy can be applied to the flowing cement. Alternatively, thermal energy can be applied from the emitter 144 and the structure 105 to the cement 150 that is introduced into the cement-carrying structure 105 but is not flowing, wherein a selected level of energy is applied and then the accelerated-polymerization cement volume is injected through the system. As can be seen in FIGS. 5C-5D, in one embodiment the controller 145 and energy source 140 are interlinked to the pressure source 160 so that variations in flow rate can modulate energy application to the cement, or the cement flow rate can be modulated to variations in the applied energy. With continued reference to FIGS. 5C-5D, in one embodiment the controller 145 can modulate energy application to the cement flow from the source 140 based at least in part on the flow rate as determined by the systems and methods described in co-pending Provisional Application No. 60/907,468 filed Apr. 3, 2007 titled Bone Treatment Systems and Methods.

Figure 6:
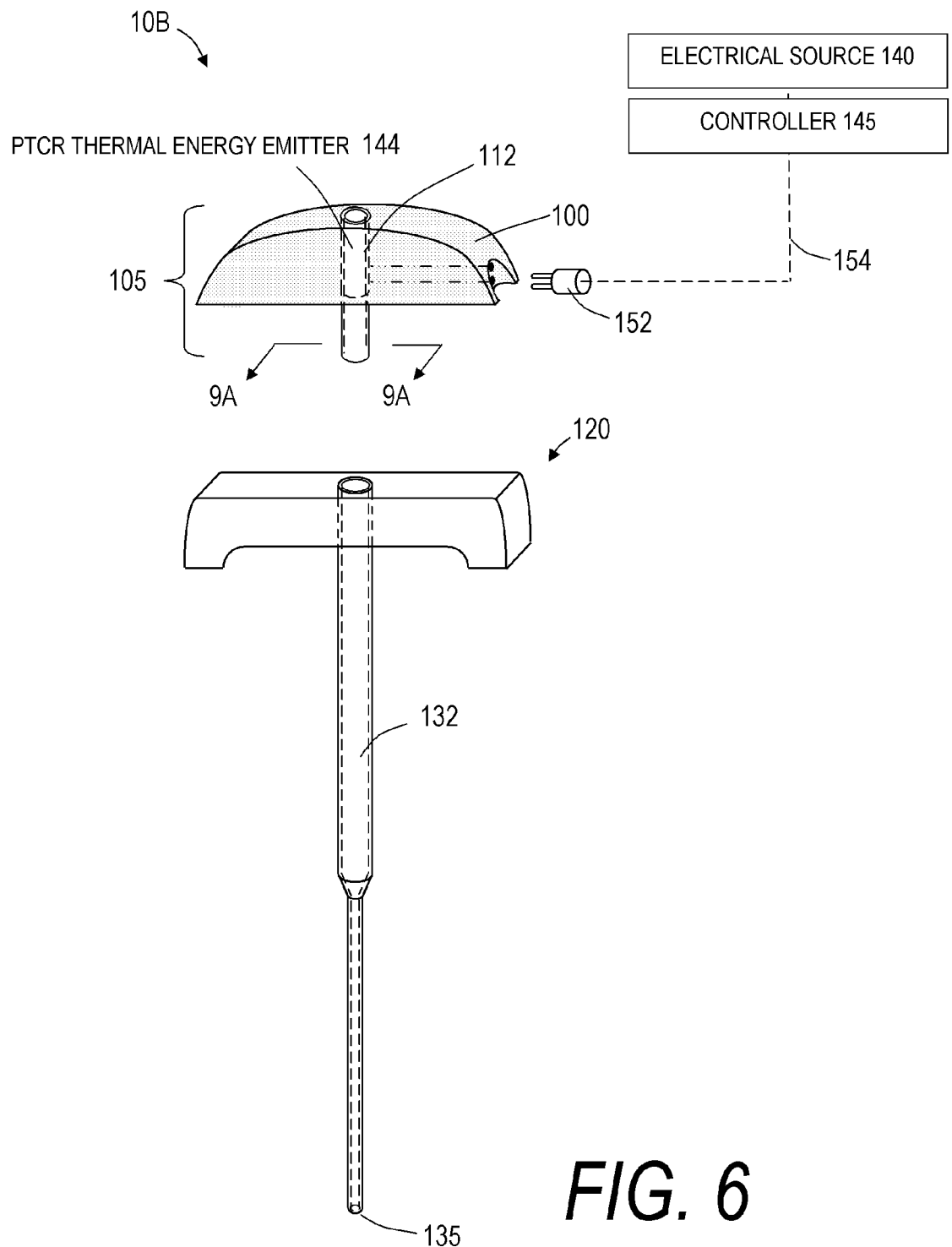
FIG. 6 is a schematic view of another embodiment of a bone cement injector system.

FIG. 6 illustrates another system embodiment 10B for use in a corresponding method which is substantially equivalent to the method depicted in FIGS. 5A-5D. As can be seen in FIG. 6, the first component indicated at 100 is similar to that of FIG. 1 except that the cement-carrying structure 105 and the PTC thermal emitter 144 are less elongated and can be detachably mated with the bone cement injector 120 as in FIGS. 1-2 and FIGS. 5A-5D. A Luer-fitting (not shown) to couple the first component 100 and the injector 120 can be used in one embodiment. It can be understood that the system embodiment 10B can apply energy to bone cement 150 that flows through the cement-carrying structure 105 and thermal emitter 144, whereas the elongated first component 100 of FIGS. 1-2 and FIGS. 5A-5D can apply energy to cement 150 that is non-flowing or flowing within the cement-carrying structure 105, or any combination of energy application intervals to non-flowing and flowing cement 150.

Figure 7:
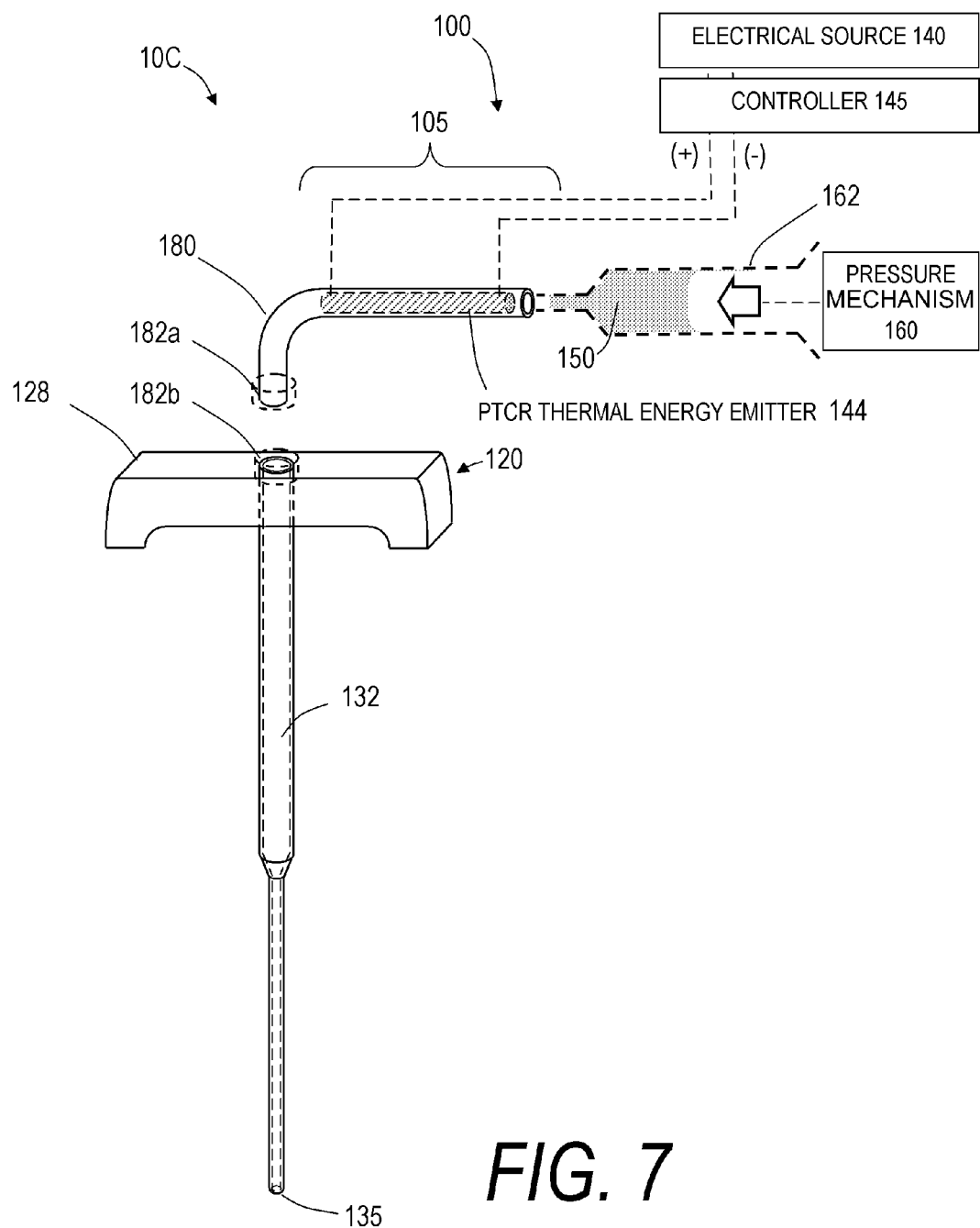
FIG. 7 is a schematic view of another embodiment of a bone cement injector system.

FIG. 7 illustrates another system embodiment 10C similar to the system of FIG. 6. The first component 100 of FIG. 7 includes the cement-carrying structure 105 and PTC thermal emitter 144 in a conduit member 180 that is proximal to the handle 128 of the bone cement injector 120 with cooperating Luer-fittings 182a and 182b for detachable mating of the components. As in the embodiment of FIG. 6, the first component 100 and thermal emitter 144 are remote from the patient's body. As in the embodiment of FIG. 6, the first component 100 of FIG. 7 and thermal emitter 144 can apply energy to cement 150 that is non-flowing within the system.

Figure 8A:
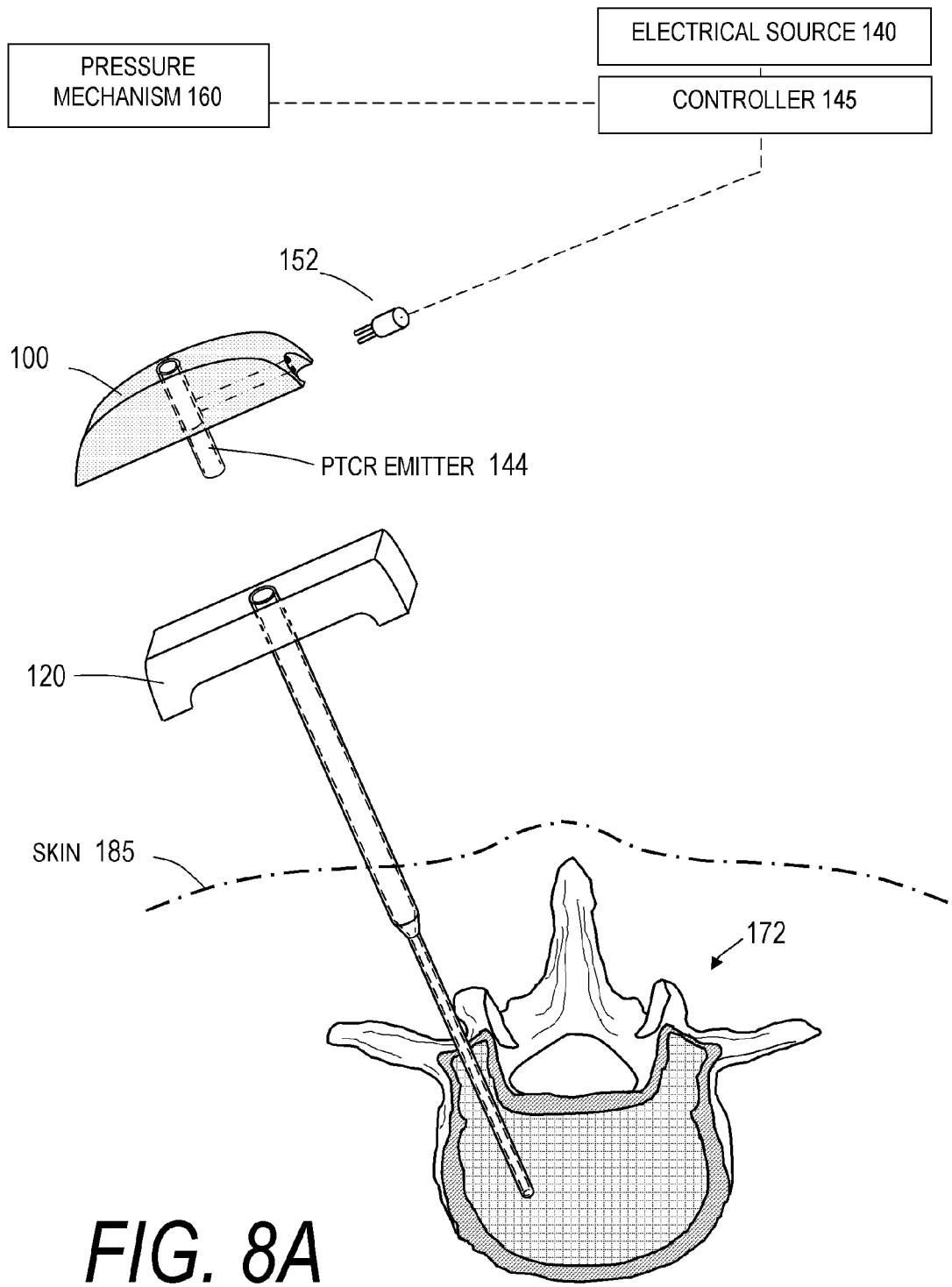
FIG. 8A is a schematic view of a step in a bone cement injection method.
Figure 8B:
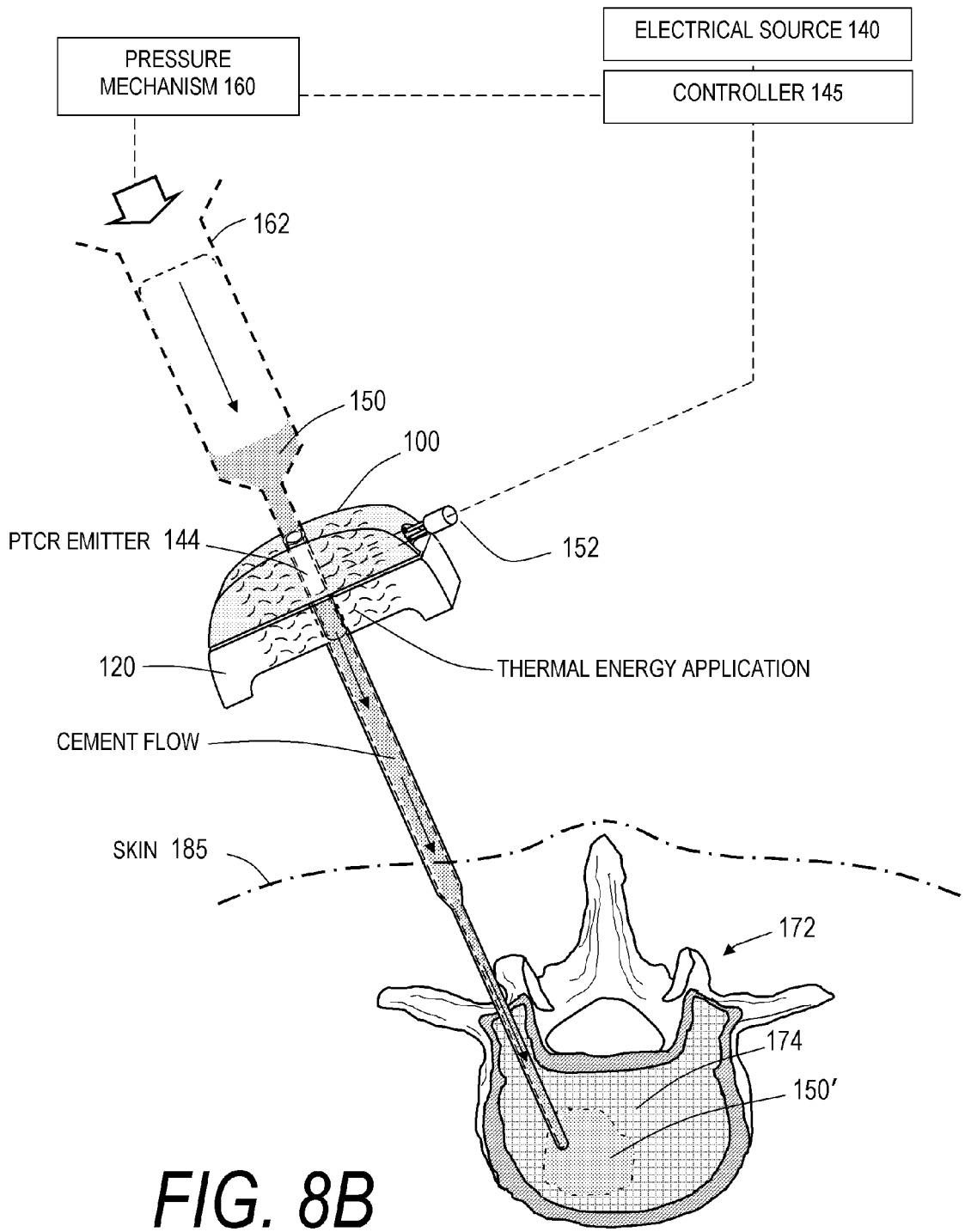
FIG. 8B is a schematic view of another step of applying energy to cement and injecting cement into a vertebra according to the bone cement injection method of FIG. 8A.

FIGS. 8A-8B graphically depict a method of the invention utilizing the system 10B of FIG. 6. It can be seen that the bone cement injector 120 of FIG. 1 is inserted into the vertebra 172 as described previously. In FIG. 8A, the first component 100 with a non-elongated cement-carrying structure 105 and thermal emitter 144 is connected to the electrical source 140 and controller 145. FIG. 8B then depicts several steps, as in FIG. 4 (and FIGS. 5B-5D), including: (i) coupling the first component 100 with the structure 105 and thermal emitter 144 to the cooperating handle portion 128 of the cement injector 120; (ii) coupling the source 162 of bone cement 150 and pressure source 160 to the cement-carrying structure 105; and (iii) injecting a flow of bone cement 150 from the source 162 through the cement-carrying structure 105 and actuating electrical source 140 and emitter 144 to apply thermal energy from the emitter 144 and structure 105 to the flow of cement 150 to thereby accelerate polymerization of the cement flow through the system, thereby providing a flow of 'accelerated-polymerization' bone cement 150' in the interior 174 of the vertebra 172. In a another step of the method as shown in FIG. 8B, the application of energy to the cement can occur when the bone cement is retained within the system, not in contact with the patient's body and outward from the patient's body or skin 185. It can be understood that a similar bone cement injection method could be used with the system 10C of FIG. 7.

Figure 9A:
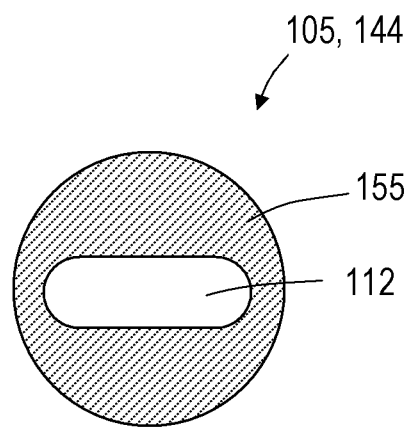
FIGS. 9A-9B are schematic cross-sectional views of one embodiment of a bone cement injector.
Figure 9B:
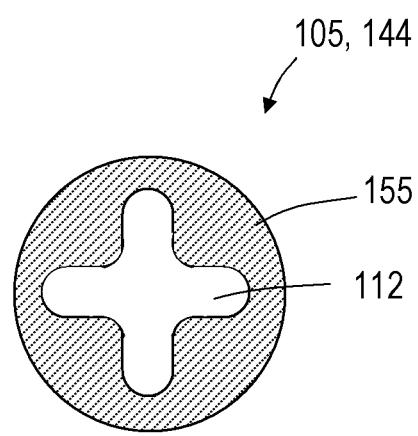

FIGS. 9A and 9B illustrate optional cross-sections of the flow channel 112 through a cement-carrying structure 105 and PTCR thermal emitter 144 or any other type of thermal emitter, with the sectional view of FIGS. 9A-9B in the exemplary embodiment of FIG. 6. It has been found that flattened or ribbon-like cement flows, as in FIG. 9A, can be most easily heated by a heating element since a larger cement surface area is exposed to the heat transferred through the wall 155 of the structure. Similarly, FIG. 9B shows another configuration of a channel 112 with a large surface area when compared to the cement flow cross-section.

Now turning to FIGS. 10A-10G, another bone cement injection method is depicted that utilizes a system similar to the system 10A of FIGS. 1 and 2. In this embodiment, a bone cement injector 120 as in FIG. 1 is inserted into a vertebra 172 as described previously. In this method which is also described by the block diagram of FIG. 4, a plurality of first components 100 (here shown as four components 100a-100d) with elongated cement-carrying structures 105 and thermal emitters 144 are used to prepare accelerated-polymerization cement 150' in advance of inserting the cement-carrying structures 105 into the bone cement injector 120. It should be appreciated that the first components 100 can number from two to ten or more, depending on their capacity and the number of vertebrae targeted for treatment. In one embodiment, the plurality of first components 100a-100d can be used to prepare accelerated-polymerization cement 150' having the same level of polymerization. In another embodiment, at least two of the plurality of first components 100a-100d can be used to prepare accelerated-polymerization cement 150' having a different level of polymerization.

Figure 10A:
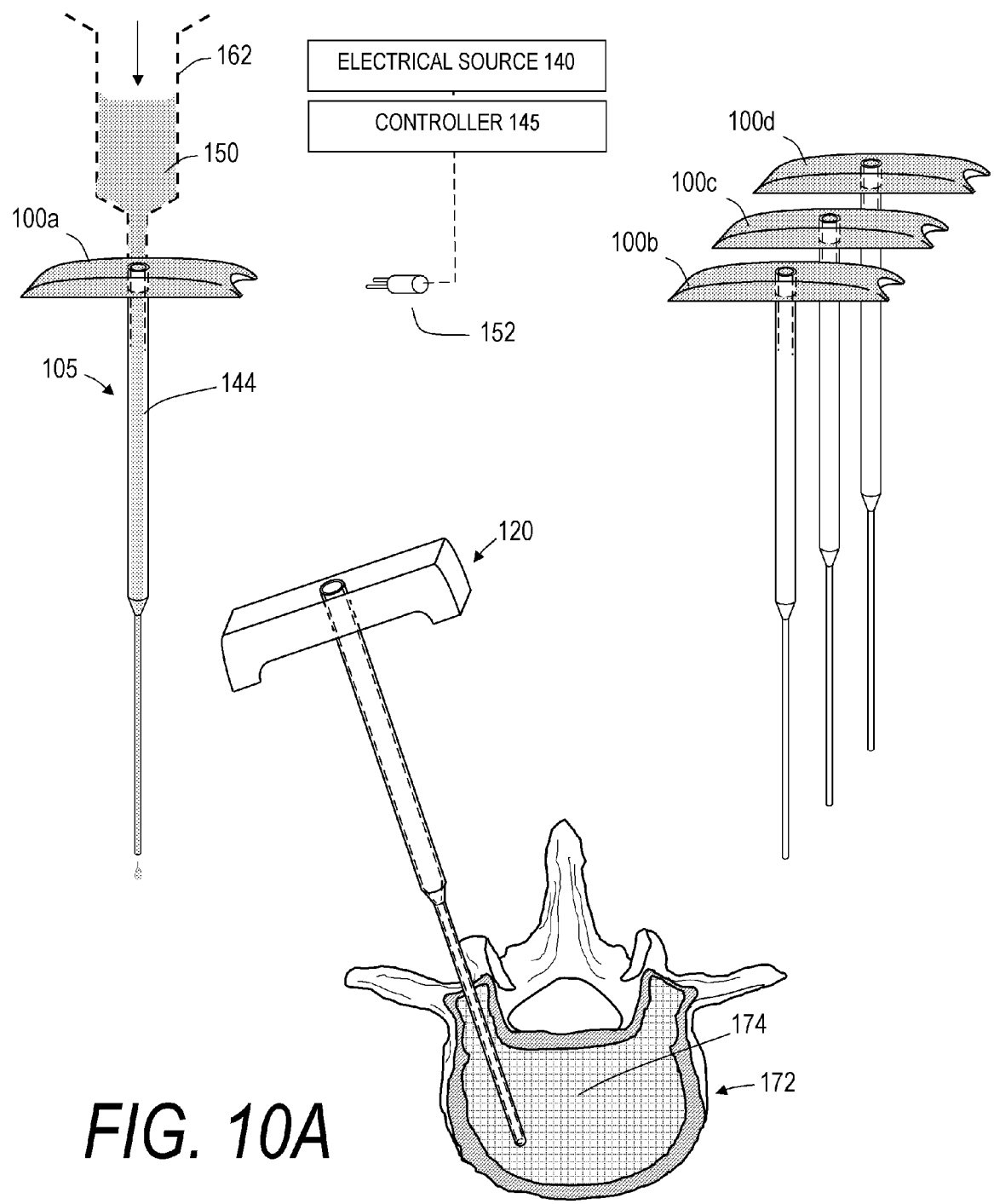
FIG. 10A is a graphical representations of a step of one bone cement injection method.
Figure 10B:
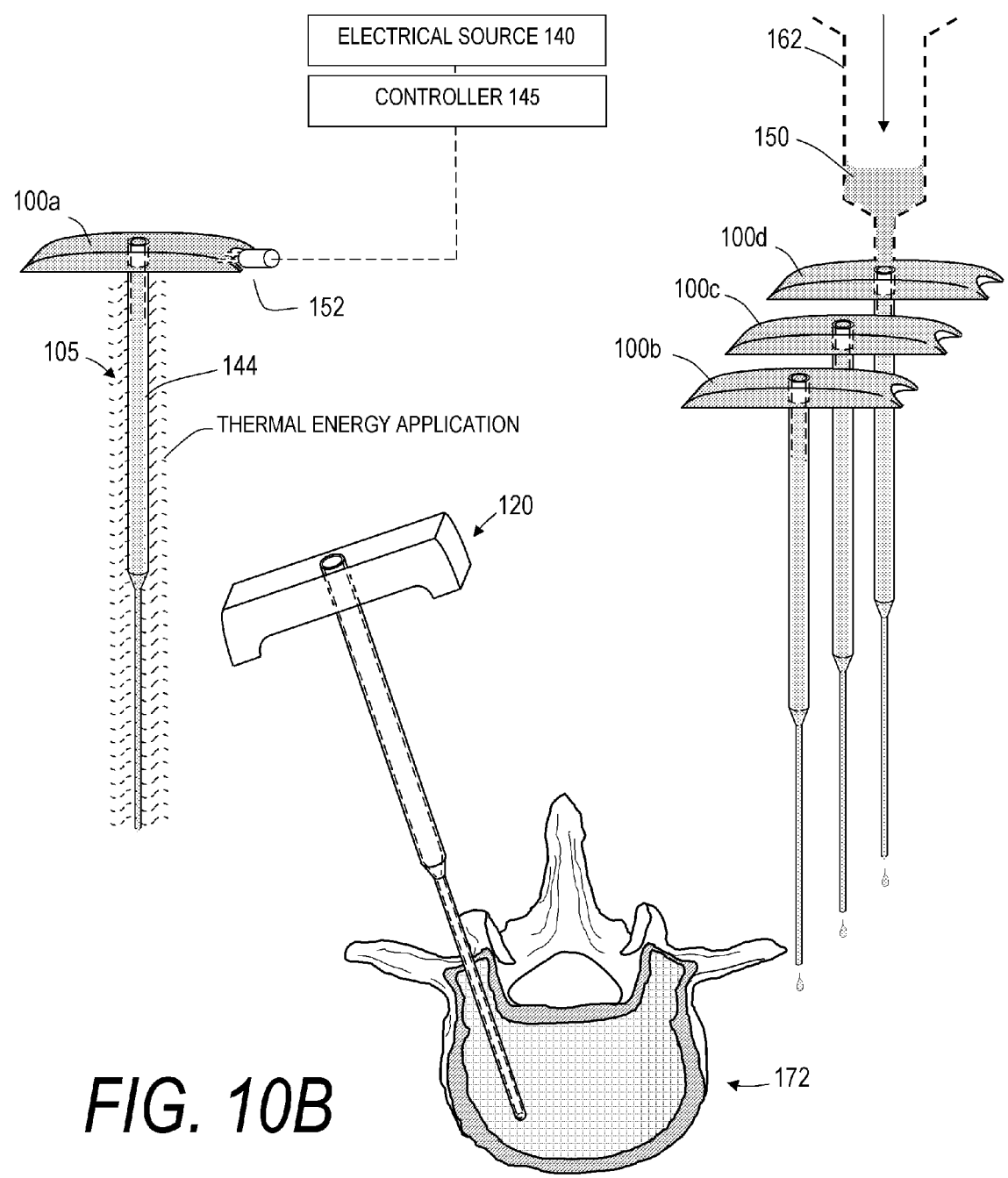
FIG. 10B is a graphical representation of another step of assembling components in the bone cement injection method.

In one step of the illustrated method, FIG. 10A illustrates filling the component 100a with a just-mixed bone cement 150, for example, from a source of bone cement such as a syringe 162. FIG. 10B next illustrates the coupling of the component 100a and the emitter 144 to the connector 152 of the electrical source 140 and controller 145. Further, FIG. 10B depicts the actuation of the electrical source 140 and controller 145 to thereby cause the energy emitter 144 (e.g., PTCR emitter) to apply thermal energy from the emitter 144 and cement-carrying structure 105 to the contained volume of cement 150 to thereby accelerate polymerization of the cement disposed within the cement carrying structure 105. FIG. 10B further illustrates filling the other components 100b-100d with the just-mixed, pre-polymerized bone cement 150 from a source or syringe 162.

Figure 10C:
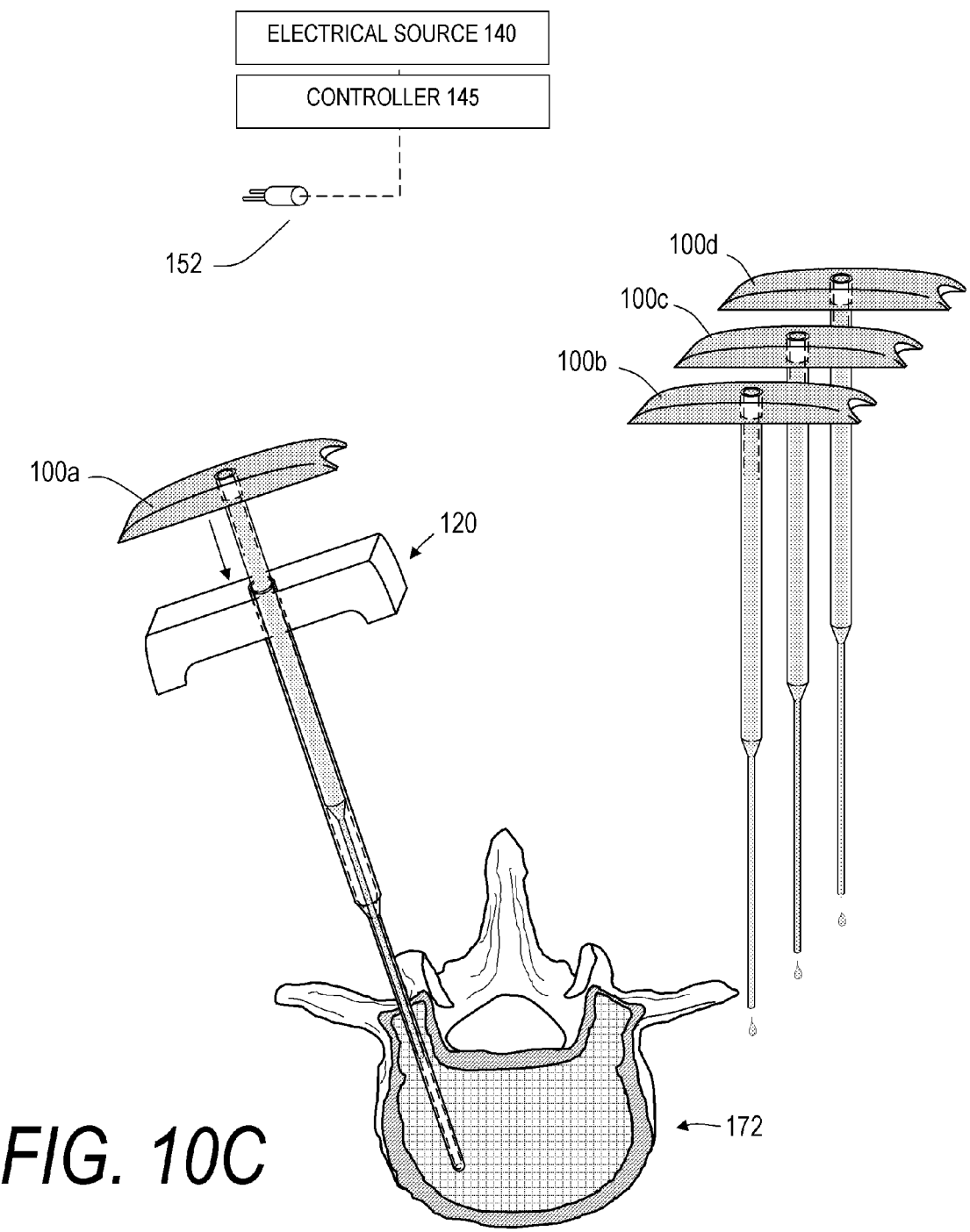
FIG. 10C is a graphical representation of another step of applying energy to cement and injecting cement into a vertebra according to the bone cement injection method.

Now referring to FIG. 10C, it can be seen that the component 100a is de-coupled from the connector 152 and the electrical source 140. Then, the component 100a is inserted into the cement injector 120, at least a portion of which has been inserted into the vertebra 172 to provide access to the vertebra 172. Thus, it can be understood that the component 100a is in operative contact with the tissue and is not connected to the energy source 140.

Figure 10D:
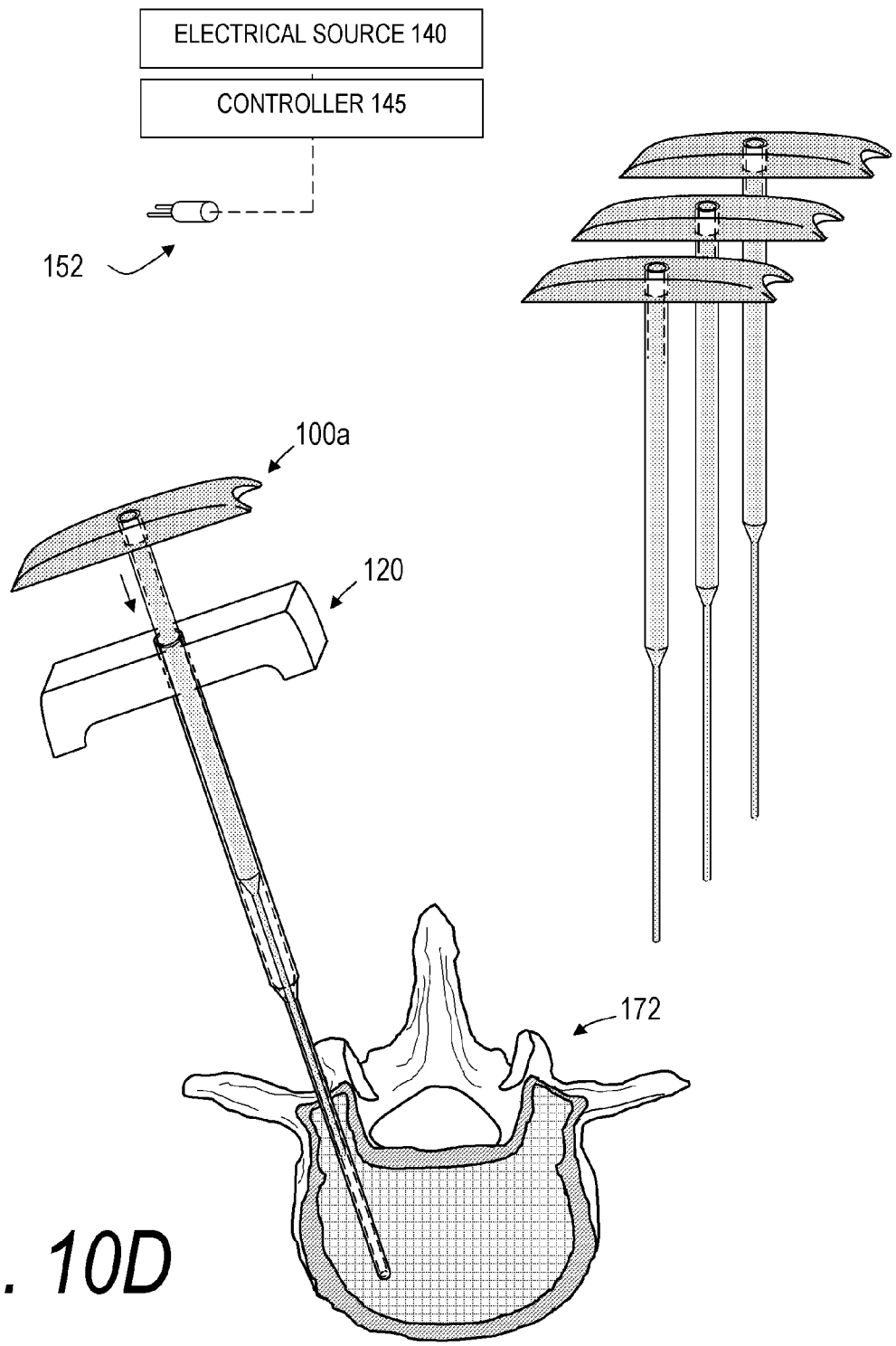
FIG. 10D is another schematic view of an injecting step of the bone cement injection method.

FIG. 10D shows another step in the illustrated embodiment in which the component 100a carrying the accelerated polymerization cement 150' is fully inserted into the cement injector 120. Further, FIG. 10E depicts coupling a pressure source 160 to the component 100a, which in one embodiment is a disposable syringe 188 filled with a predetermined volume of saline or any biocompatible fluid or gel 190 having a volume that approximates the volume of cement 150' carried within the component 100a, or at between 50% and 99% of said cement volume, or between 75% and 90% of said cement volume, or at less than 50% of said cement volume.

Figure 10E:
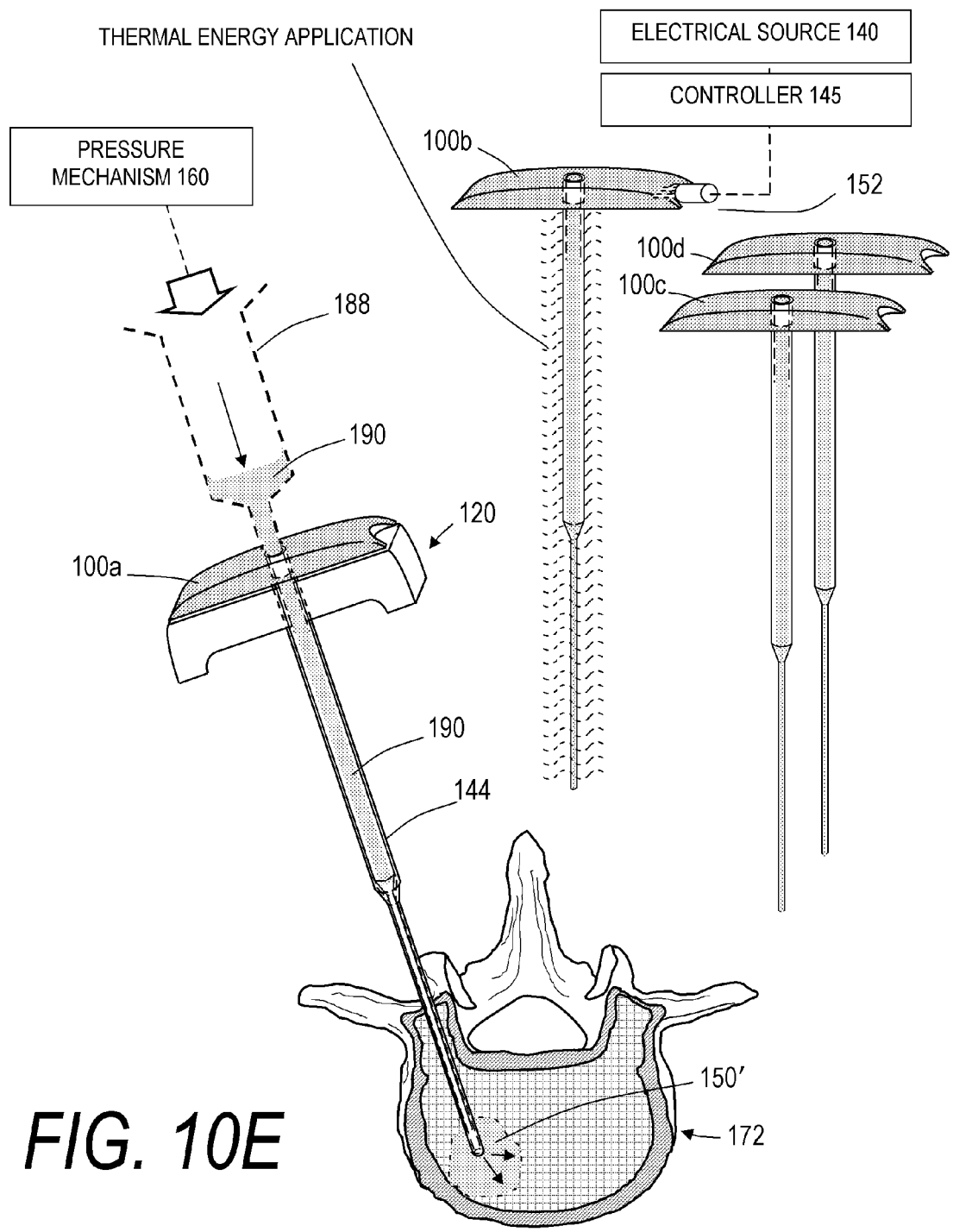
FIG. 10E is a schematic view of preparing a second injector according to one embodiment of the bone cement injection method.

FIG. 10E illustrates another step where the actuation of the pressure source 160 causes the gel 190 to be introduced into the component 100a to displace the accelerated polymerization cement 150' and inject said cement 150' into the interior 174 of the vertebra 172. As in previous methods, the method of FIGS. 10-10E thus provides a modified volume of the cement 150' that first contacts bone having an 'accelerated-polymerization' state with a selected viscosity range that substantially prevents cement extravasation. FIG. 10E further illustrates coupling a component 100b to a connector 152 and an electrical source 140, and also depicts the actuation of the electrical source 140 and emitter 144 to apply thermal energy to the contained volume of cement 150 within the component 100b.

Figure 10F:
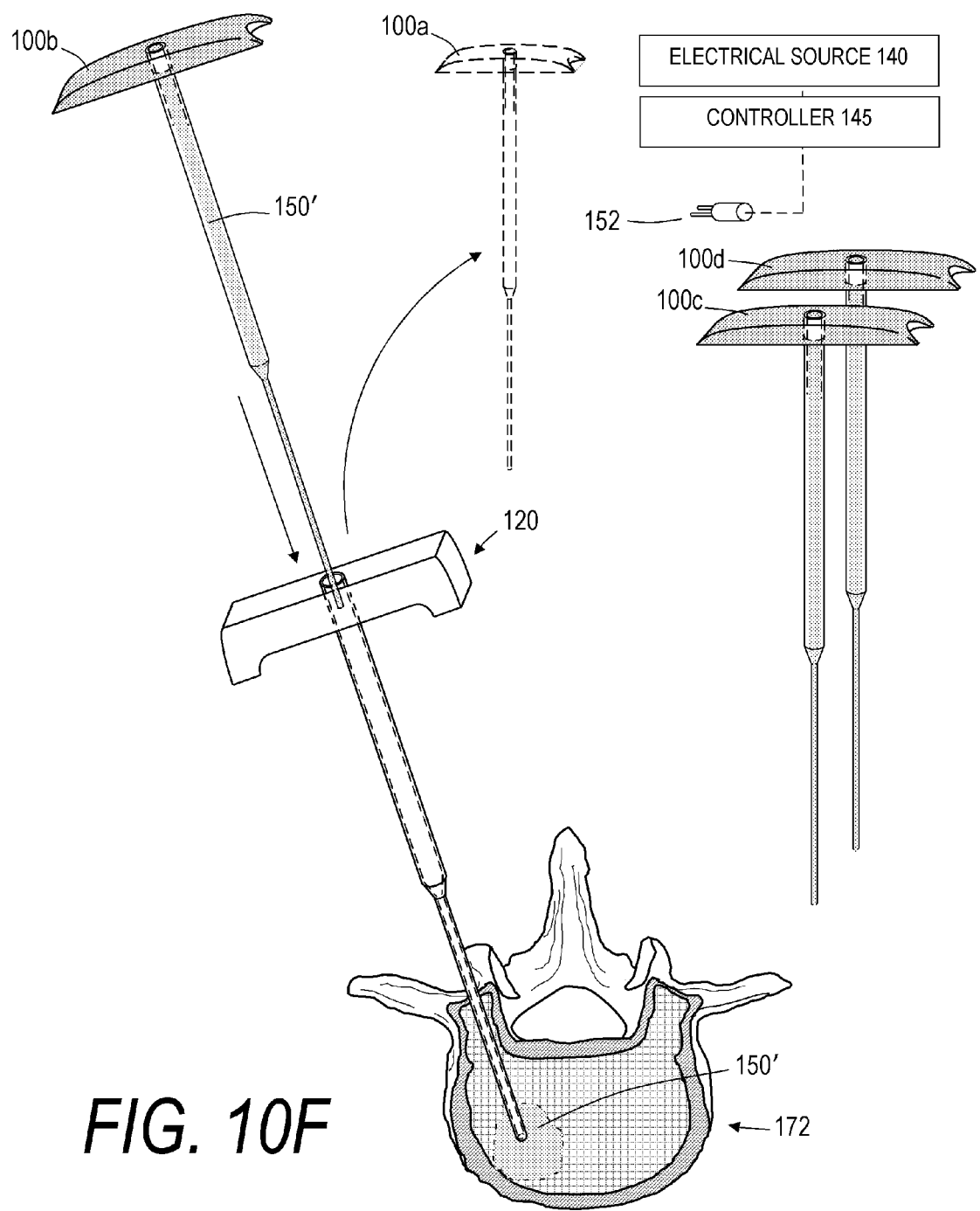
FIG. 10F is another schematic view of preparing the second injector according to the bone cement injection method.
Figure 10G:
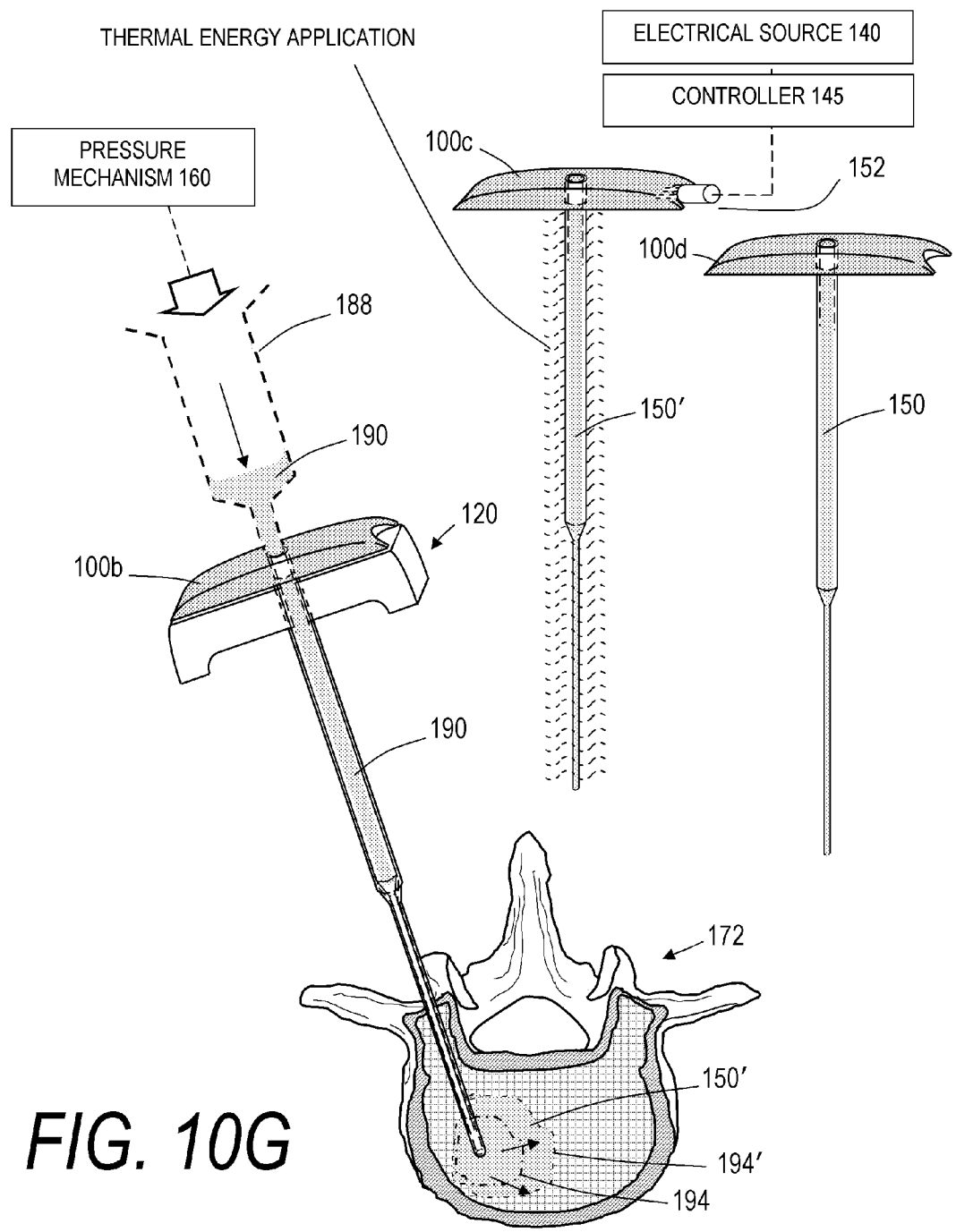
FIG. 10G is a schematic view of an injecting step according to the bone cement injection method.

FIG. 10F illustrates the removal of the empty component 100a from the cement injector 120 and further depicts de-coupling the component 100b from the connector 152 and electrical source 140, and the partial insertion of that cement-filled component 100b into the cement injector 120. FIG. 10G next illustrates another step in the illustrated embodiment in which the coupling and actuation of the pressure source 160 to the component 100b to thereby introduce an additional volume of accelerated polymerization cement 150' into the interior 174 of the vertebra 172. It can be seen in FIG. 10G that the cement volume in the vertebra has increased in perimeter from 194 to 194'. The additional volumes of cement in the components, indicated by 100c and 100d, of FIG. 10G can be utilized as described above to accelerate the polymerization with each component, and then sequentially inject the cement volumes or portions thereof into bone.

Figure 11:
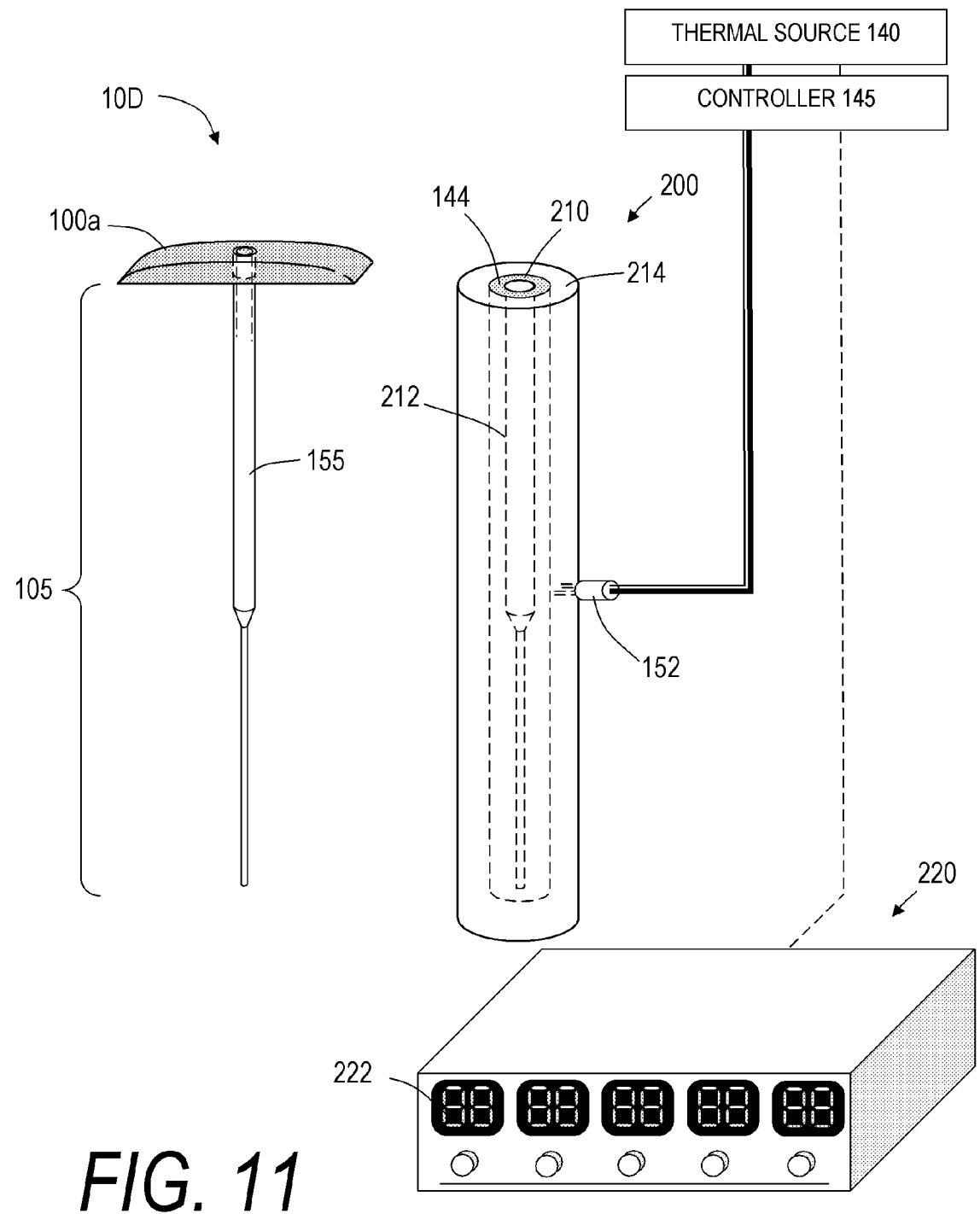
FIG. 11 is a schematic view of another embodiment of a bone cement injector system.

FIG. 11 illustrates another embodiment or system 10D that is similar to that of FIGS. 1-2 that is utilized to perform the method of FIG. 4 and FIGS. 10A-10G. The embodiment of FIG. 11 differs only in that the thermal energy emitter 144 is not carried in the wall 155 of the first component 100a'. In the embodiment depicted in FIG. 11, the thermal energy emitter 144 (e.g., a PTCR emitter, as described above) can be removably disposed within a disposable or non-disposable body or housing 200 (e.g., disposed within a recess in the housing 200). The housing 200 can receive and engage the wall 155 of the first component 100a' and cement-carrying structure 105'. In the embodiment of FIG. 11, a thermal energy emitter 144 is within a core body portion 210 of the housing 200, which has a receiving bore 212 for receiving the elongated cement-carrying structure 105' of the first component 100a'. The core body portion 210 can be surrounded by an insulative body portion 214. In one embodiment, the core body portion 210 and thermal energy emitter 144 can be configured substantially as the heat emitter of FIG. 3, with optional thicker cross-sections. In FIG. 11, it can be seen that the body 200 and emitter 144 can again be coupled to the connector 152, electrical source 140 and controller 145.

FIG. 11 illustrates another component of system 10D (which also can be linked to the systems 10A-10C) that can include a data acquisition system 220 and display(s) 222 coupleable to the controller 145, wherein the data acquisition system 220 receives a signal of at least one polymerization parameter of the accelerated polymerization cement 150' within the system and displays said at least one polymerization parameter in the display(s) 222. For example, the emitter 144 can function as an electrode to sense said at least one polymerization parameter, said sensed parameter transmitted to the data acquisition system 220 via a signal from the emitter 144 through the controller 145 to the data acquisition system 220. In one embodiment, the data and signal system 220 can provide at least one of: (i) the time interval remaining to a selected polymerization endpoint, (ii) the calculated cement viscosity, (iii) the cement temperature, (iv) the rate of change of the temperature or viscosity, (v) the acceleration or rate of change of the cement temperature or viscosity, (vi) the elapsed time since energy was applied to the cement, and (vii) the amount of energy applied to the cement. In the embodiment illustrated in FIG. 11, the data and signal system 220 has at least one visual display indicated at 222, but the signal communicated by the data acquisition system 220 can also be an aural signal, a tactile signals and the like.

Figure 12A:
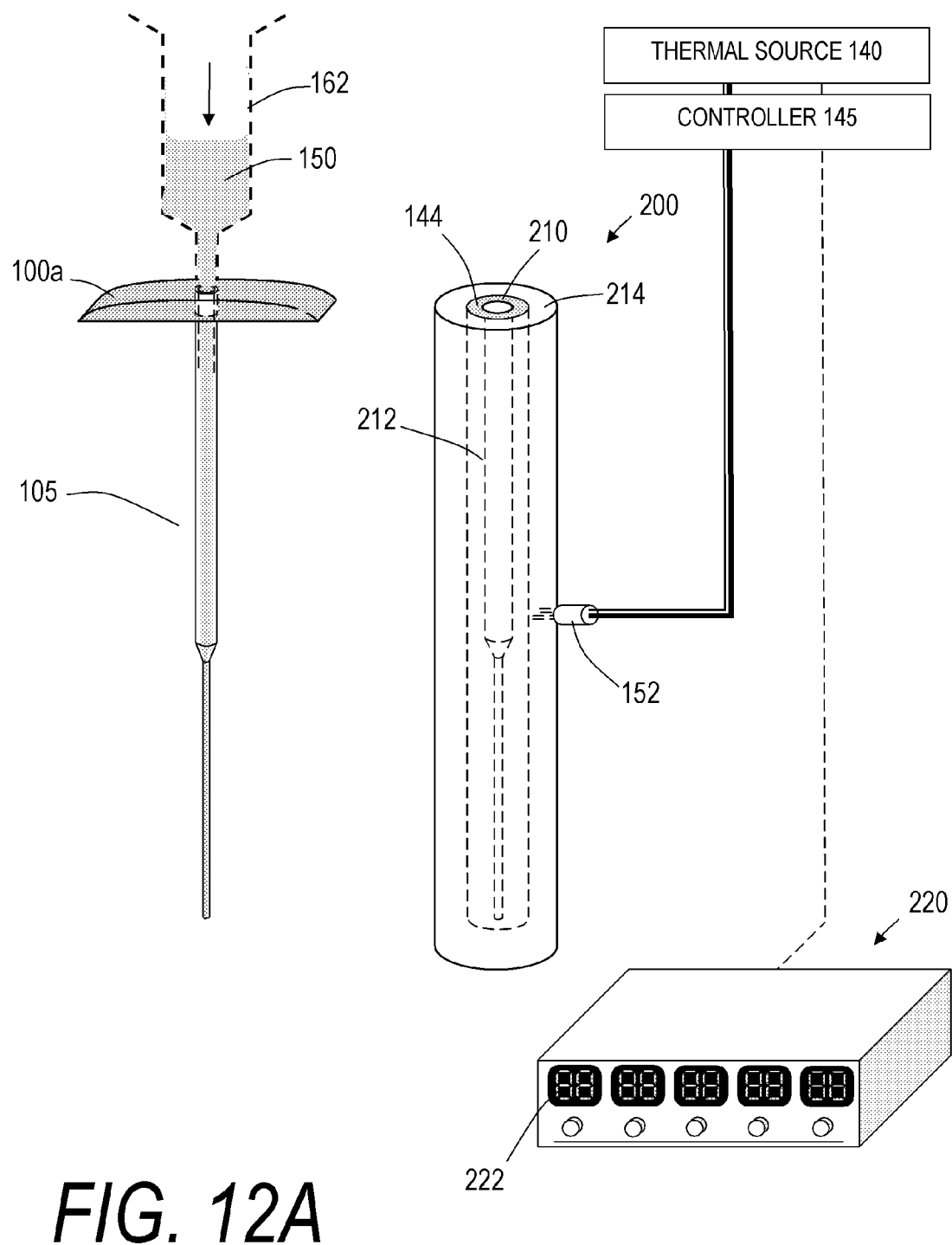
FIG. 12A is a graphical representation of one step of a bone cement injection method.
Figure 12B:
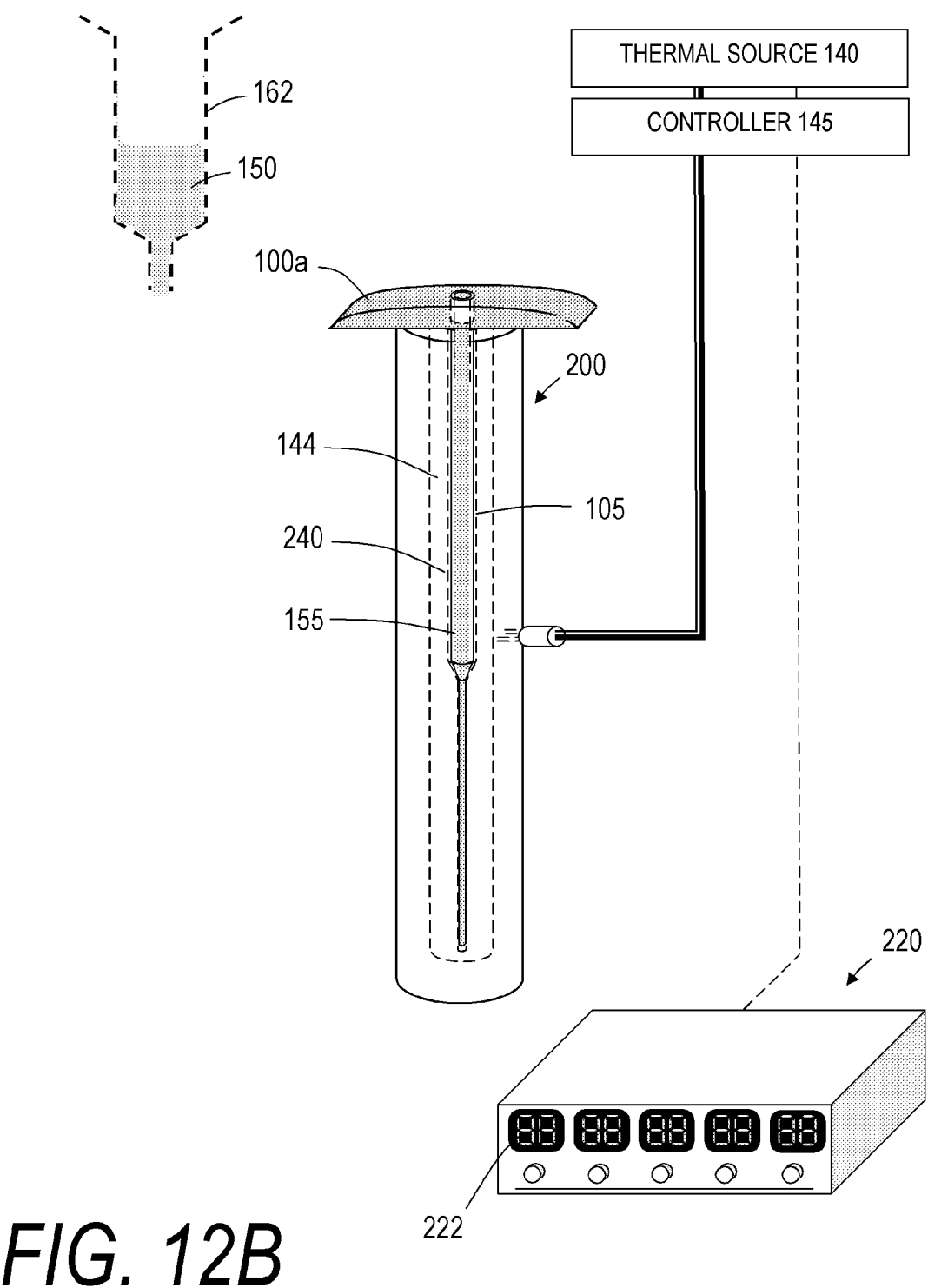
FIG. 12B is a graphical representation of another step of assembling components of the bone cement injector system.

FIGS. 12A-12D depict a method of use of system 10D, which is similar to the method of FIGS. 10A-10G, so that each step of this method need not be repeated in detail. FIG. 12A illustrates filling the first component 100a' with a just-mixed bone cement 150, such as PMMA, from a cement source 162. FIG. 12B depicts de-coupling the cement source 162 from the first component 100a', and then inserting the cement-carrying structure 105' into the receiving channel 212 of the body 200 that carries the thermal emitter 144.

Figure 12C:
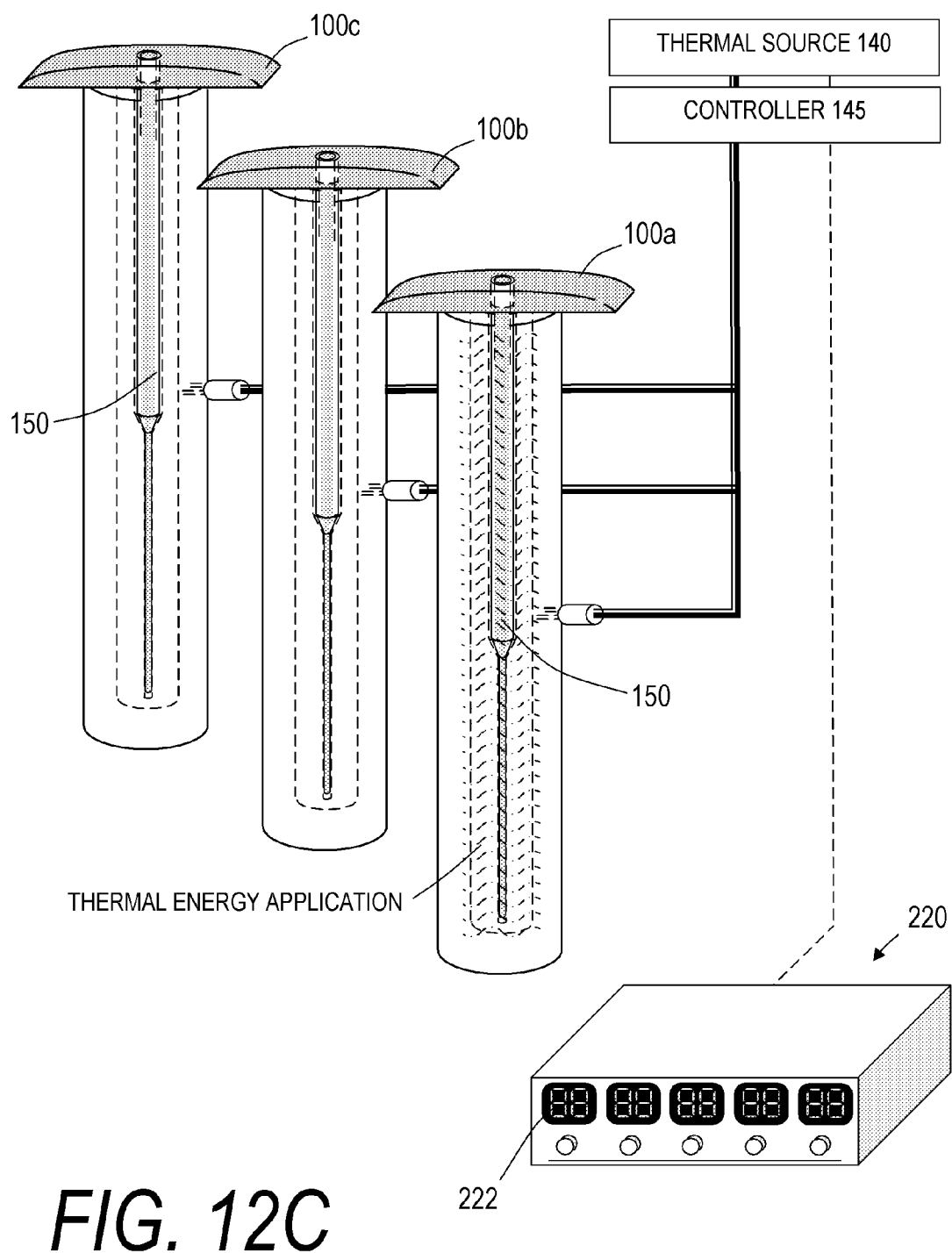
FIG. 12C is a graphical representation of another step of applying energy to cement and injecting cement into a vertebra according to the bone cement injection method.

FIG. 12C depicts the steps of filling a plurality of components 100a'-100c with cement 150, and then inserting at least one in a thermal energy application body 200, as in FIG. 10B. FIG. 12C further depicts actuating the electrical source 140 and controller 145 to thereby cause the thermal emitter 144 in each of the bodies 200 to apply thermal energy from the emitter 144 to the engaged cement-carrying structure 105' to the contained volume of cement 150 to thereby accelerate polymerization of the cement 150. In one embodiment, the controller 145 can control the application of energy from the thermal energy emitters so that substantially the same level of energy is transmitted to the bon cement 150 in the bodies 200 via the respective emitters in the bodies 200. In another embodiment, the controller 145 can control the application of energy from the thermal energy emitters so that different levels of energy are transmitted from the emitters in the respective bodies 200 to the bone cement 150 in the components 100a'-100c disposed in the bodies 200.

Figure 12D:
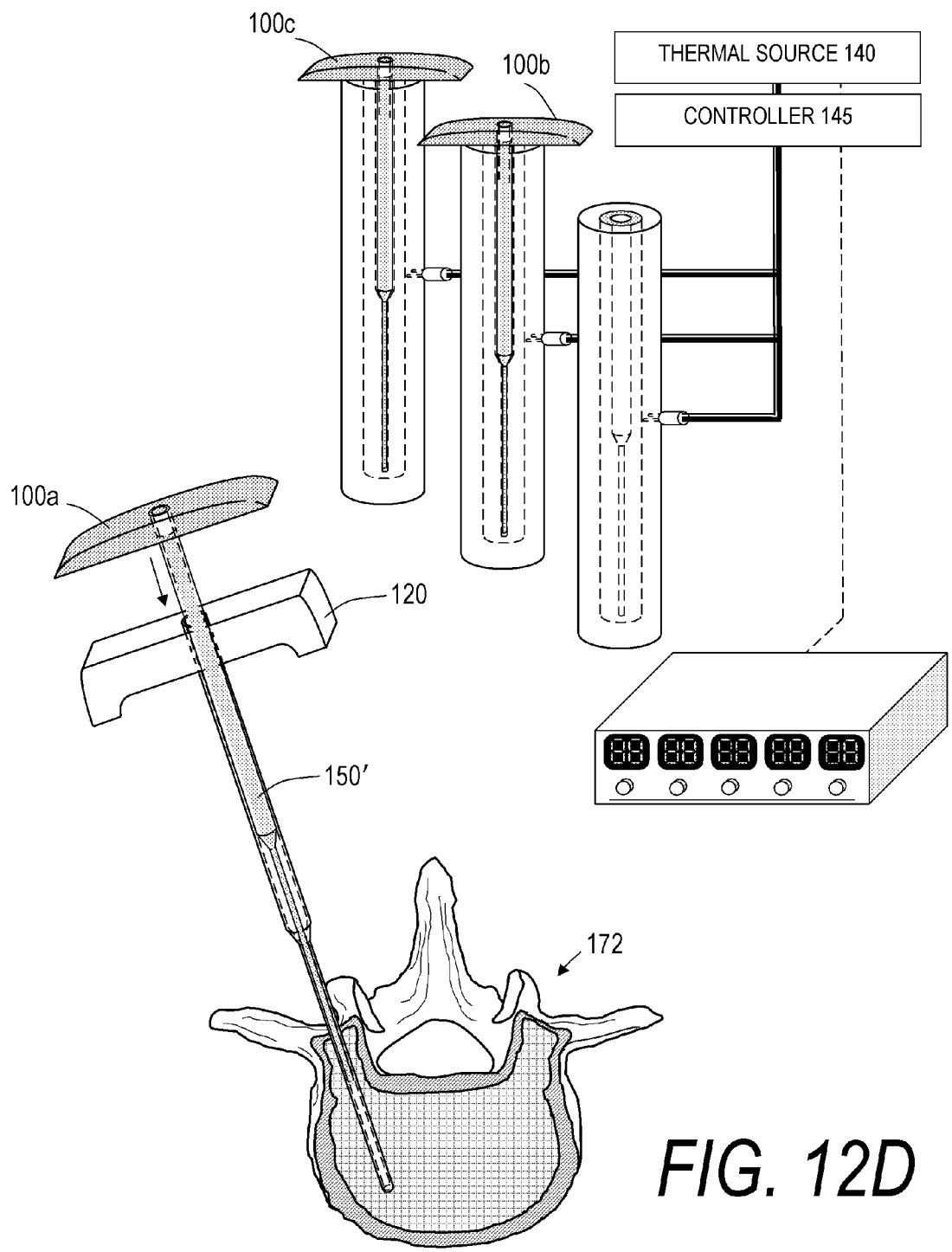
FIG. 12D is another schematic view of the injecting step of the bone cement injection method.

FIG. 12D then illustrates removing a component 100a' from the body 200 and inserting the component 100a' that then carries the accelerated polymerization cement 150' into the cement injector 120. As can be understood, the subsequent steps of FIGS. 10D-10G need not be repeated in the drawings. A pressure source 160 can be coupled to a component 100a' to introduce the cement 150' into the bone, and the sequence is followed with additional volumes of accelerated polymerization cement. During the sequential treatment and introduction of the cement 150' into the vertebra, the display(s) 222 can inform the physician of operational and polymerization parameters of the cement, and the physician can utilize the controller to apply energy to the cement to thus allow for the accelerated polymerization cement 150' to have substantially the same viscosity cement to be used throughout a procedure, even if the procedure may last 30 minutes, 60 minutes or more. The system and energy source 140 can preferably apply energy of at least 0.01 Watt, 0.05 Watt, 0.10 Watt, 0.50 Watt and at least 1.0 Watt. In another aspect, the energy source and controller are configured for accelerating the polymerization rate of the bone cement to a selected endpoint in less than 1 second, 5 seconds, 10 seconds, 20 seconds, 30 seconds, 45 seconds, 60 seconds and 2 minutes.

The system of FIGS. 11-12D can use any energy source as a thermal emitter 144, such as a recirculating non-ambient temperature fluid source, a radiofrequency source, an electrical source, a resistive heat source, a positive temperature coefficient of resistance (PTCR) constant temperature heat source, a non-coherent light source, a laser source, a LED source, a microwave source, a magnetic source and an ultrasound source. In summary, one embodiment of the invention comprises at least one cement-carrying structure 105' for carrying pre-polymerized bone cement 150, the structure releasably coupleable with a bone cement injector 120; and an energy source 140 operatively coupleable to the structure 105' for causing controlled thermal effects in the bone cement therein for accelerating the polymerization thereof. The emitter 144 and energy source 140 can be carried by the cement-carrying structure 105', or the thermal energy emitter component 144 can be within an assembly with a receiving portion 132 that receives the cement-carrying structure 105'. The system has a controller 145 that can controllably apply energy to at least one of a flow of cement and non-flowing cement 150. In another embodiment, the cement-carrying structure 105' can include a flexible sleeve, a rigid sleeve, a bladder, a syringe, a tube, a conduit, a bellows, a non-compliant sac or balloon, a compliant sac or balloon, and an elastomeric thin-wall member, any of which can be coupled to a cement injector 120. It should be appreciated that, in one embodiment, the body 200 also can carry a cooling system for decelerating polymerization of the cement 150 contained within the cement carrying structure 105' disposed within the body 200, and one bone cement injection method using the systems disclosed above can include accelerating polymerization of the cement 150 and then stalling or decelerating polymerization by cooling the cement 150 to maintain the cement generally in a ready state for use by the physician. Accordingly, the cooling system can be used to maintain the bone cement 150 in a predetermined state (e.g., at a generally constant temperature or viscosity), thereby extending the working time of the cement 150. Any suitable cooling system known in the art may be used, such as circulation of a cooling fluid or cryogenic fluid. A further discussion of bone treatment systems and methods, including cooling systems, can be found in U.S. patent application Ser. No. 11/469,769 filed Sep. 1, 2006, the entire contents of which are hereby incorporated by reference and should be considered a part of this specification.

The cooling system can be an active cooling system or a passive cooling system. In one embodiment (not shown), the cooling system can includes a thermoelectric system with at least one element (e.g., a Peltier element) in contact with a thermally conductive wall portion of the thermal energy application body. In another embodiment (not shown), the cooling system can include a chilled fluid circulation system with channels disposed proximate the wall portion of thermal energy application body. In another embodiment (not shown) the cooling system can include a Freon system with an expansion channel inside the wall portion of the thermal energy application body. However, the cooling system can include other suitable active cooling arrangements. In still another embodiment (not shown), the cooling system can include a heat pipe system with at least one elongate channel or concentric channel in the wall portion of the thermal energy application body, which wicks heat away from the thermal energy application body to a heat exchanger component. In yet another embodiment (not shown), the cooling system can be a passive system that includes an open cell graphite structure for conducting heat away from the thermal energy application body to a heat exchanger component. In such an embodiment, the open cell graphite can be Poco-Foam™ manufactured by Poco Graphite, Inc. 300 Old Greenwood Road, Decatur, Tex. 76234.

In one embodiment as in FIG. 11, the body 200 for receiving the cement-carrying structure 105' has a cooperating bore 212 that can provide a wall-to-wall interface 240 (FIG. 12B) between the wall of the emitter 144 that substantially contacts and engages the wall 155 of the cement-carrying structure 105' to provide heat transfer thereto. In other embodiments, the interface 240 can be a fluid interface with the wall 155, a gel or elastomer interface with the wall 155, or heated gas or vapor interface with the wall 155. Further, the body 200 (not shown) can have a plurality of receiving portions 132 for receiving any rigid, flexible or bladder-type cement-carrying structure 105'.

In another aspect of the invention, a method for bone cement injection in an osteoplasty procedure comprises (a) providing a bone cement injector body 120 carrying a PTCR or NTCR material (positive temperature coefficient of resistance or negative temperature coefficient of resistance); (b) causing cement flow through the injector body 120; and (c) measuring an electrical parameter of the PTCR or NTCR material in response to heat transfer from the cement flow to the PTCR or NTCR material to thereby determine a selected parameter of the cement flow. It has been found that the change in impedance of the temperature coefficient material can be used to accurately determine the flow rate of the cement flow. In turn, the signals can indicate a measurement of impedance, or change in impedance over an interval, or the rate of change of impedance of the temperature coefficient material to determine the viscosity of the cement within the cement flow proximate to the PTCR material or at the flow outlet.

In another aspect of the invention, the method of bone cement injection can include modulating the rate of cement flow in response to determining a selected parameter of the cement flow such as flow rate. The method of bone cement injection can further include applying and modulating a thermal energy application from an emitter in the injector body to the cement flow. The method of bone cement injection can further include modulating the application of energy in response to signals that relate to a selected parameter such as flow rate of the cement flow.

Of particular interest, another method of bone cement injection can include (a) providing a bone cement injector body 120 carrying a PTCR (positive temperature coefficient of resistance) material in a flow channel therein, (b) applying a selected level of energy to a cement flow through the PTCR material, and (c) utilizing an algorithm that processes impedance values of the PTCR material to determine the cement flow rate. The method of bone cement injection further includes modulating a cement injection parameter in response to the processed impedance values.

Of particular interest, another method of bone cement injection can include (a) providing a bone cement injector body 120 carrying a PTCR material or other thermal energy emitter in a flow channel therein, (b) causing a selected cement flow rate and a selected level of energy delivery to the cement flow through the emitter, and (c) modulating the selected flow rate and/or energy delivery to maintain a substantially constant impedance value of the emitter material over a cement injection interval. The selected cement injection interval can be at least 1 minute, at least 5 minutes, at least 10 minutes and at least 15 minutes. In another aspect of the invention, the method modulates the selected flow rate and/or energy delivery to maintain a substantially constant viscosity of bone cement injected from the injector 120 over a cement injection interval. The system and energy source 140 is configured for applying energy of at least 0.01 Watt, 0.05 Watt, 0.10 Watt, 0.50 Watt and at least 1.0 Watt. However, the system and energy source 140 can in one embodiment apply more than 1.0 Watt. In another aspect, the energy source 140 and controller 145 can accelerate the polymerization rate of the bone cement 150 to a selected (e.g., predetermined) endpoint in less than 1 second, 5 seconds, 10 seconds, 20 seconds, 30 seconds, 45 seconds, 60 seconds and 2 minutes.

In another embodiment of the invention, the accelerated polymerization cement 150' of FIGS. 12A-12D can be further "pre-treated" by the body 200 or prior to introduction into the cement-carrying structure 105' to provide a cement 150 in the form of an emulsion. By the term emulsion, it is meant that a cement 150 such as PMMA is mixed with another biocompatible fluid that is not well absorbed in the cement 150 such as saline solution. In one embodiment, it has been found that a uniform PMMA-saline emulsion can be created by mechanical activation of the just-mixed PMMA components together with a saline solution. Such an emulsion can be created by stirring the components with a paddle at a relatively high speed, e.g., a small paddle at at least 100 rpm, 500 rpm, 1000 rpm, 5000 rpm, and 10,000 rpm. It has been found that the final modulus of such a cured polymer emulsion may be useful for supporting a vertebra 172 as the modulus is somewhat less than a conventional non-emulsion PMMA.

Another method of bone cement injection can utilize an apparatus as describe above and comprises (a) providing a bone cement injector body 120 with a flow channel 112 extending therethrough from a proximal handle end 116 though a medial portion to a distal end portion having a flow outlet, (b) causing cement flow through the flow channel, and (c) warming the cement flow with an energy emitter 144 in a proximal end or medial portion thereof to initiate or accelerate polymerization of the cement 150 of the cement flow to a selected (e.g. predetermined) level. The method includes providing a flow rate of the cement flow that ranges from 0.1 cc/minute to 20 cc/minute, from 0.2 cc/minute to 10 cc/minute, and from 0.5 cc/minute to 5 cc/minute.

Of particular interest, the above-described method of bone cement injection can allow a predetermined cement flow rate to provide a selected interval in which the cement flows is allowed to polymerize in the flow channel downstream from the energy emitter. This method includes providing a selected interval of greater than 1 second, greater than 5 seconds, greater than 10 seconds, greater than 20 seconds, and greater than 60 seconds.

The above-described method utilizes an energy emitter 144 that applies energy sufficient to elevate the temperature of the bone cement 150 by at least 1° C., at least 2° C., and at least 5° C. The method of bone cement injection includes utilizing an energy emitter 144 that applies at least 0.1 Watt of energy to the cement flow, at least 0.5 Watt of energy to the cement flow, and at least 1.0 Watt of energy to the cement flow. The method includes the flow rate of the cement flow being adjusted in intervals by controller 145, or being continuously adjusted by a controller 145.

The above description of certain embodiments of the invention is intended to be illustrative and not exhaustive. Particular characteristics, features, dimensions and the like that are presented in dependent claims can be combined and fall within the scope of the invention. The invention also encompasses embodiments as if dependent claims were alternatively written in a multiple dependent claim format with reference to other independent claims. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

Of course, the foregoing description is that of certain features, aspects and advantages of certain embodiments of the present invention, to which various changes and modifications can be made without departing from the spirit and scope of the present invention. Moreover, the bone treatment systems and methods need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A system for treating bone, comprising: two or more elongated cement-carrying devices configured to receive a volume of mixed bone fill material therein; two or more sleeves, each sleeve configured to removably receive at least a portion of an elongated cement-carrying device of the two or more elongated cement-carrying devices in an receiving channel thereof; a controller configured to control the polymerization rate of the mixed bone fill material such that the mixed bone fill material of at least two of the two or more elongated cement-carrying devices have different viscosities; wherein each of two or more sleeves further comprises an energy emitter, wherein the controller is configured to control the application of energy from the energy emitters so that different levels of energy are transmitted from the emitters to the mixed bone fill material in the two or more elongated cement-carrying devices disposed in the two or more sleeves; and an elongated bone fill material injector, wherein the elongated bone fill material injector is sized to receive an elongated cement-carrying device of the two or more elongated cement-carrying devices therein.

2. The system of claim 1, wherein at least one sleeve of the two or more sleeves further comprises an energy emitter configured to apply energy to the mixed bone fill material in the cement-carrying device disposed in the at least one sleeve.

3. The system of claim 2, further comprising an energy source coupleable to the energy emitter to deliver energy thereto.

4. The system of claim 2, wherein the energy emitter is separate from the two or more elongated cement-carrying devices.

5. The system of claim 1, wherein at least one sleeve of the two or more sleeves further comprises a cooling system configured to retard the polymerization rate of the mixed bone fill material in the cement-carrying device disposed in the at least one sleeve.

6. The system of claim 1, further comprising a bone fill source.

7. The system of claim 1, wherein each elongated cement-carrying device has a corresponding sleeve.

8. The system of claim 1, further comprising a data acquisition system that communicates with the controller, wherein the data acquisition system is configured to provide information indicative of the viscosity of the mixed bone fill material.

* * * * *